(12) United States Patent
Phan et al.

(10) Patent No.: US 6,569,836 B2
(45) Date of Patent: May 27, 2003

(54) 6-O-ALKYL-2-NOR-2-SUBSTITUTED KETOLIDE DERIVATIVES

(75) Inventors: Ly Tam Phan, Malden, MA (US); Yat Sun Or, Cambridge, MA (US); Zhenkun Ma, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/727,934

(22) Filed: Nov. 30, 2000

(65) Prior Publication Data

US 2002/0103140 A1 Aug. 1, 2002

Related U.S. Application Data

(60) Provisional application No. 60/168,504, filed on Dec. 2, 1999.

(51) Int. Cl.$^7$ .......................... A61K 31/70; C07H 17/08
(52) U.S. Cl. ............................ 514/29; 536/7.2; 536/7.4
(58) Field of Search ............................ 514/29; 536/7.2, 536/7.4

(56) References Cited

U.S. PATENT DOCUMENTS

| | | | |
|---|---|---|---|
| 4,331,803 A | 5/1982 | Watanabe et al. ............ 563/7.2 |
| 4,670,549 A | 6/1987 | Morimoto et al. ............ 536/7.4 |
| 4,874,748 A | 10/1989 | Katz et al. ..................... 514/29 |
| 4,990,602 A | 2/1991 | Morimoto et al. ............ 563/7.4 |
| 5,444,051 A | 8/1995 | Agouridas et al. ............. 514/29 |
| 5,561,118 A | 10/1996 | Agouridas et al. ............. 514/29 |
| 5,770,579 A | 6/1998 | Agouridas et al. ............. 514/29 |
| 5,866,549 A | 2/1999 | Or et al. ......................... 514/29 |

FOREIGN PATENT DOCUMENTS

| | | |
|---|---|---|
| EP | 260938 | 12/1992 |
| WO | 93/21200 | 4/1992 |
| WO | 98/30574 | 7/1998 |
| WO | 99/21871 | 5/1999 |

OTHER PUBLICATIONS

James B. McAlpine, et al. *Journal of Antibiotics*, XL(8) 1115–1122 (1987).

*Primary Examiner*—Charanjit S. Aulakh
(74) *Attorney, Agent, or Firm*—B. Coregory Donner

(57) ABSTRACT

The present invention relates to 6-O-alkyl-2-nor-2-substituted ketolide compound or a derivative thereof, a composition comprising the compound and a suitable carrier, a method of preparing the compound, and a method of treatment and prevention of in mammals comprising administering said compound.

12 Claims, No Drawings

6-O-ALKYL-2-NOR-2-SUBSTITUTED KETOLIDE DERIVATIVES

This application claims the benefit of U.S. Provisional Application No. 60/168,504, filed Dec. 2, 1999.

TECHNICAL FIELD

The present invention relates to a novel macrolide compound or a pharmaceutically acceptable salt, ester, solvate or prodrug thereof; a composition comprising the compound and a suitable carrier; a method of preparing the compound; and a method of treatment and prevention of infections in a mammal comprising administering the compound.

BACKGROUND OF THE INVENTION

Erythromycins A, B, C and D, represented by the formula below,

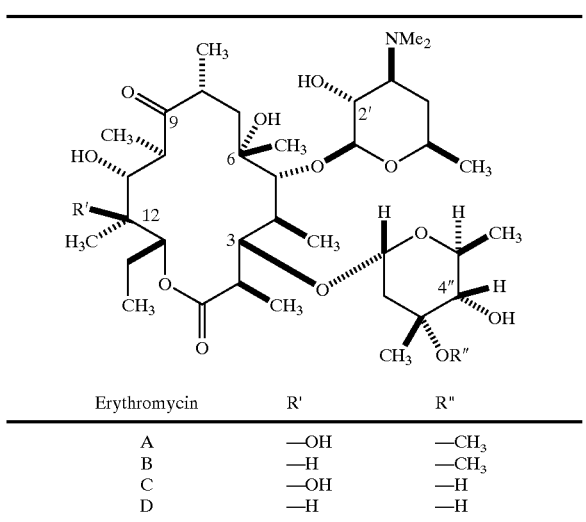

| Erythromycin | R' | R" |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

U.S. Pat. No. 4,874,748 describes a 2-norerythromycin D derivative, which were produced in a strain *Streptomyces erythreus* 12693-240 transformed by pNJI bearing DNA from *Streptomyces antibioticus*. The potential of using genetic engineering techniques to produce novel members of the commercially important class of antibiotics, the macrolides, was demonstrated by James B. McAlpine et al., *Journal of Antibiotics*, XL(8) 1115–1122 (1987). These processes provide structurally determined 2-norerythromycin derivatives, however the antibacterial activities of 2-norerythromycins A, B, C and D can be somewhat disappointing.

PCT Publication No. WO 99/21871, published on May 6, 1999, describes the 2-position of a 3,9-diketo-6—O-substituted tricyclic imine or carbamate can be substituted with a halogen. The C-2 carbon of the 2-substituted 3,9-diketo-6—O-substituted tricyclic imine or carbamate is substituted with a methyl and a halogen atom selected from fluorine, chlorine, bromine or iodine.

Copending U.S. patent application Ser. No. 09/312,517, filed May 14, 1999, discloses C-2 modified erythromycin derivatives wherein the C-2 carbon of a 6—O-substituted ketolide derivative has been substituted with methyl and a substituent selected from substituted alkyl, substituted or unsubstituted alkenyl, and substituted or unsubstituted alkynyl.

U.S. Pat. Nos. 5,561,118; 5,770,579 and 5,444,051 describe erythromycin derivatives having C-2 substitution with methyl and a substituent selected from hydrogen, alkyl and alkylamine.

SUMMARY OF THE INVENTION

The invention relates to a new class of macrolide compounds having antibacterial activity. Novel modifications of the C2-position of compounds of the invention provide a new class of 6—O-alkyl-2-nor-2-substituted ketolide derivatives. The compounds can be prepared via C2-derivatization of a 2-norerythromycin fermentation product or the 2-methyl group of an erythromycin derivative can be removed by new methods and further derivatized to afford the desired C2-derivatization. Pharmaceutical compositions and a method of treatment are also described herein.

In one aspect, therefore, the present invention relates to compounds selected from the group consisting of:

a compound of formula

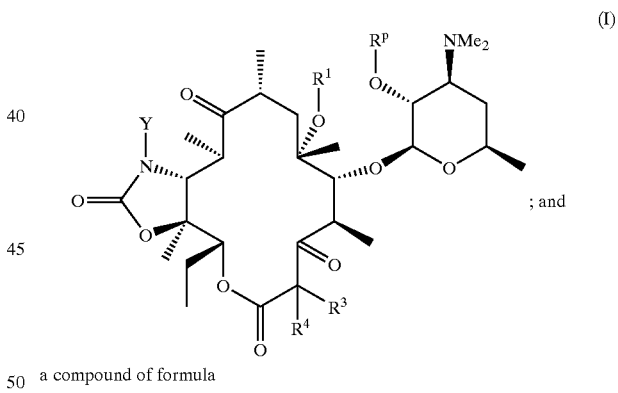

(I)

; and a compound of formula

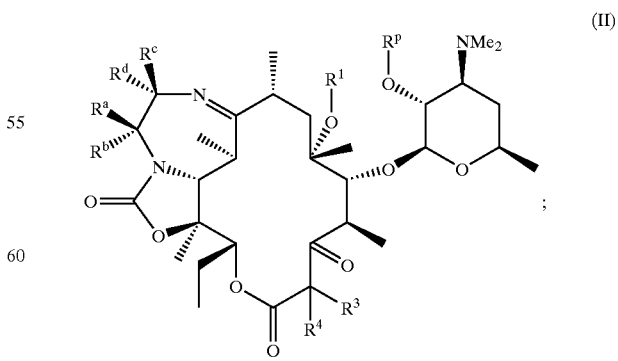

(II)

;

or a pharmaceutically acceptable salt, ester, solvate or prodrug thereof, wherein:

$R^p$ is hydrogen or a hydroxy protecting group;
$R^1$ is selected from the group consisting of:
  (a) $C_1$–$C_6$ alkyl optionally substituted with one or more substituents selected from the group consisting of:
    (i) hydroxy;
    (ii) —CH=O;
    (iii) aryl;
    (iv) substituted aryl;
    (v) heteroaryl;
    (vi) substituted heteroaryl;
    (vii) $Ar_1$–$Ar_2$, wherein $Ar_1$ and $Ar_2$ are independently selected from the group consisting of aryl, substituted aryl, heteroaryl, and substituted heteroaryl; and
    (viii) —NR'R", wherein R' and R" are independently selected from the group consisting of hydrogen and $C_1$–$C_6$ alkyl, or wherein R' and R" are taken with nitrogen atom to which they are connected to form a 3- to 7-membered ring optionally containing a hetero function selected from the group consisting of —O—, —NH—, —N($C_1$–$C_6$-alkyl-)—, —N(aryl-$C_1$–$C_6$-alkyl-), —N(substituted aryl-$C_1$–$C_6$-alkyl-)—, —N(heteroaryl-$C_1$–$C_6$-alkyl-)—, and —N(substituted heteroaryl-$C_1$–$C_6$-alkyl-)—;
  (b) $C_1$–$C_6$-alkenyl;
  (c) $C_1$–$C_6$-alkenyl-$R^2$;
  (d) $C_1$–$C_6$-alkynyl; and
  (e) $C_1$–$C_6$-alkynyl-$R^2$;
$R^2$ is selected from the group consisting of:
  (a) hydrogen;
  (b) aryl;
  (c) substituted aryl;
  (d) heteroaryl;
  (e) substituted heteroaryl; and
  (f) $Ar_1$–$Ar_2$, wherein $Ar_1$ and $Ar_2$ are as defined above;
$R^3$ is selected from the group consisting of:
  (a) hydrogen;
  (b) OH;
  (c) F, Cl, Br or I;
  (d) $C_1$-alkyl substituted with one or more substituents selected from the group consisting of:
    (i) aryl;
    (ii) substituted aryl;
    (iii) heteroaryl;
    (iv) substituted heteroaryl;
    (v) —NR'R", wherein R' and R" as defined above; and
    (vi) —$OR^5$, wherein $R^5$ is hydrogen or $C_1$–$C_6$ alkyl optionally substituted with one or more substituents selected from the group consisting of:
      (1) aryl;
      (2) substituted aryl;
      (3) heteroaryl; and
      (4) substituted heteroaryl;
    (vii) —OC(O)$R^5$, wherein $R^5$ is as defined above;
  (e) $C_2$–$C_6$ alkyl optionally substituted with one or more substituents selected from the group consisting of:
    (i) aryl;
    (ii) substituted aryl;
    (iii) heteroaryl;
    (iv) substituted heteroaryl;
    (v) —NR'R", wherein R' and R" as defined above;
    (vi) —$OR^5$, wherein $R^5$ is as defined above; and
    (vii) —OC(O)$R^5$, wherein $R^5$ is as defined above;
  (f) $C_1$–$C_6$-alkenyl;
  (g) $C_1$–$C_6$-alkenyl-$R^2$, wherein $R^2$ is as defined above;
  (h) $C_1$–$C_6$-alkynyl;
  (i) C—$C_6$-alkynyl-$R^2$, wherein $R^2$ is as defined above;
  (j) —$OR^5$, wherein $R^5$ is as defined above;
  (k) —OC(O)$R^5$, wherein $R^5$ is as defined above;
  (l) —$CH_2SO_2NHR^5$, wherein $R^5$ is as defined above;
  (m) —$CH_2S(O)_xR^5$, wherein x is 0,1 or 2, and $R^5$ is as defined above; and
  (n) —$CH_2NHR^5$, wherein $R^5$ is as defined above;
$R^4$ is selected from the group consisting of:
  (a) hydrogen;
  (b) OH;
  (c) $NH_2$;
  (d) $NHR^5$, wherein $R^5$ as defined above;
  (e) PhSe;
  (f) F, Cl, Br or I,
or $R^3$ and $R^4$ taken together with the atoms to which each is attached forms a 3- to 6-membered aromatic or non-aromatic ring optionally containing a heteroatom, wherein the non-aromatic ring optionally contains one to two double bonds or $R^3$ and $R^4$ taken together form a =$CH_2$ (exocyclic methylene), —$CH_2O$— (epoxide) or =O (oxo);
$R^a$, $R^b$, $R^c$ and $R^d$ are independently selected from the group consisting of:
  (a) hydrogen;
  (b) $C_1$–$C_6$ alkyl, optionally substituted with one or more substituents selected from the group consisting of:
    (i) —L—M—$R^6$, wherein
    L is either absent or selected from the group consisting of:
      (1) —C(O)NH—;
      (2) —NHC(O)—;
      (3) —NH—;
      (4) —N($CH_3$)—;
      (5) —O—;
      (6) —S(O)$_x$—, wherein x is 0, 1, or 2;
      (7) —C(=NH)NH—;
      (8) —NHC(=NH)—;
      (9) —C(O)O—;
      (10) —OC(O)—;
      (11) —OC(O)NH—;
      (12) —NHC(O)O—; and
      (13) —NHC(O)NH—;
    M is either absent or selected from the group consisting of:
      (1) —($CH_2$)$_1$—, wherein 1 is 1 to 5,
      (2) —($CH_2$)$_m$—CH=CH—, wherein m is 0 to 3,
      (3) —($CH_2$)$_n$—C≡C— wherein n is 0 to 3;
    $R^6$ is selected from the group consisting of:
      (1) hydrogen,
      (2) aryl,
      (3) substituted aryl,
      (4) heteroaryl,
      (5) substituted heteroaryl, and
      (6) $Ar_1$–$Ar_2$, wherein $Ar_1$ and $Ar_2$ are independently selected from the group consisting of:
        (a) aryl,
        (b) substituted aryl,
        (c) heteroaryl, and
        (d) substituted heteroaryl; and
    (ii) halogen;
  (c) $C_3$–$C_7$ cycloalkyl;
  (d) heterocycloalkyl; and
  (e) substituted heterocycloalkyl;

or any one pair of substituents selected from the group consisting of $R^aR^b$, $R^aR^c$, $R^aR^d$, $R^bR^c$, $R^bR^d$, and $R^cR^d$ taken together with the atom or atoms to which they are attached form a 3- to 7-membered ring optionally containing a hetero function selected from the group consisting of —O—; —NH—; —N($C_1$-$C_6$ alkyl-)—; —N(aryl-$C_1$-$C_6$ alkyl-)—; —N(substituted aryl-$C_1$-$C_6$ alkyl-)—; —N(heteroaryl-$C_1$-$C_6$ alkyl-)—; —N(substituted heteroaryl-$C_1$-$C_6$ alkyl-)—; —S(O)$_x$—, wherein x is as defined above; —C(O)—NH—; —NH—C(O)—; —C(O)—NR—; and —$NR^{12}$—C(O)—; wherein $R^{12}$ is hydrogen, $C_1$-$C_3$ alkyl, $C_1$-$C_3$ alkyl substituted with aryl, substituted aryl, heteroaryl, or substituted heteroaryl; and Y is selected from the group consisting of:
(a) hydrogen,
(b) $NH_2$;
(c) OH;
(d) Z—$R^7$, wherein Z is selected from the group consisting of:
  (i) —NH—$(CH_2)_p$—, wherein p is 0 to 5;
  (ii) —$(CH_2)_p$—, wherein p is as defined above;
  (iii) —NH—$C_1$-$C_5$ alkene-;
  (iv) -$C_1$-$C_5$ alkene-;
  (v) —NH—$C_1$-$C_5$ alkyn-, and
  (vi) —$C_1$-$C_5$ alkyn-; and $R^7$ is selected from the group consisting of:
  (i) hydrogen;
  (ii) aryl; (iii) substituted aryl;
  (iv) heteroaryl;
  (v) substituted heteroaryl, and
  (vi) $Ar_1$-$Ar_2$, wherein $Ar_1$ and $Ar_2$ are as defined above.

In another aspect, the invention relates to a process for preparing a compound of formula (I) or (II) comprising the steps of:
(a) treating a compound of the formula:

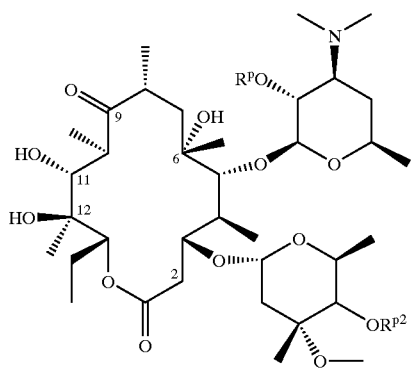

(III)

wherein $R^p$ and $R^{p2}$ are independently selected from the group consisting of hydrogen and a hydroxy protecting group, under suitable conditions for:
  (i) protecting the 2'- and optionally the 4"-hydroxy groups;
  (ii) converting the C9-carbonyl into a C9-oxime;
  (iii) alkylating the 6—O-hydroxy; (iv) optionally deprotecting the 2'- and 4"-hydroxy groups;
  (v) deoximating the C9-oxime;
  (vi) removing the 3-cladinose sugar and oxidizing the resulting 3-hydroxy group; and
  (vii) preparing a 10,11-anhydro-12-acylimidazolyl derivative of the compound to afford a compound of the formula:

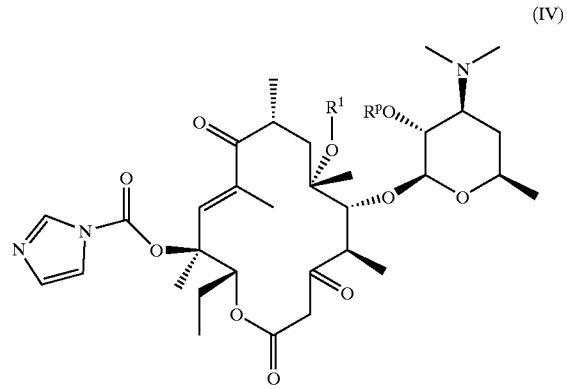

(IV)

(b) treating the compound obtain in step (a) with ammonia, ammonia hydroxide, a primary amine of the formula Y'—$NH_2$, wherein Y' is Z—$R^7$ and Z and $R^7$ are as defined above, or a diamine of the formula:

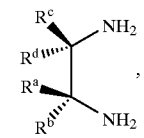

wherein $R^a$, $R^b$, $R^c$ and $R^d$ are as defined above, to provide a compound of the formula:

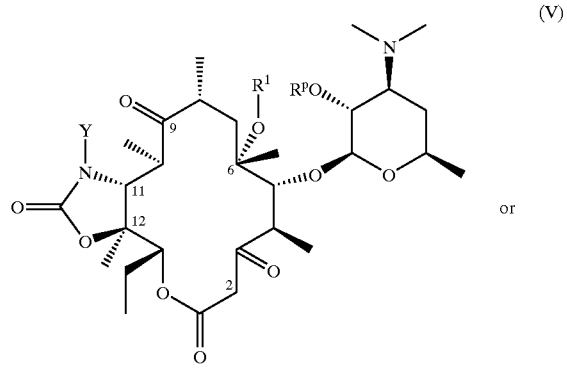

(V)

or

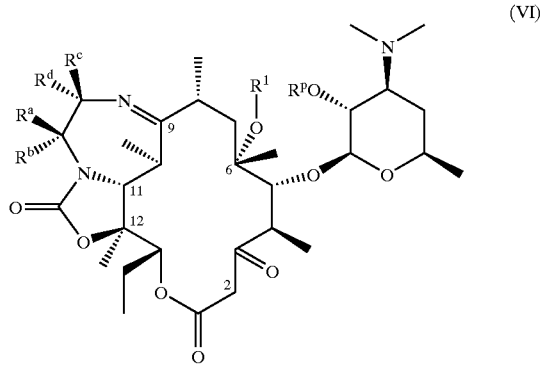

(VI)

wherein Y, $R^1$, $R^a$, $R^b$, $R^c$, $R^d$, and $R^p$ are as previously defined;
(c) derivatizing the C2-position of a compound of formula (V) or (VI) in one of the following manners:

(i) alkylation with a C, N, S, or O electrophile;

(ii) oxidation of a compound obtained from step (c)(i);

(iii) alkylation of a compound obtained from step (c)(i);

(iv) treating the compound obtained in step (c)(ii) with a carbon, nitrogen, sulfur, or oxygen nucleophile; and (v) replacing one or both C2-hydrogen atoms with a halogen atom; and (d) optionally removing any hydroxy protecting group that may be present.

In another aspect, the invention relates to a process for preparing a compound of formula (I) or (II), as defined above, comprising the steps of:

(a) treating a compound of the formula:

(VII)

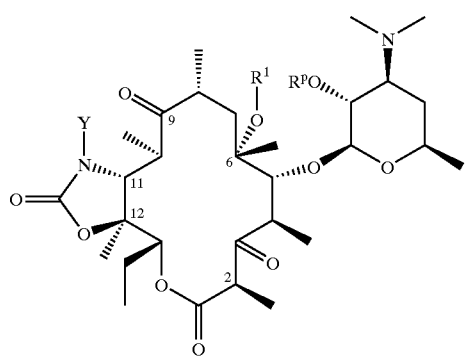

or (VIII)

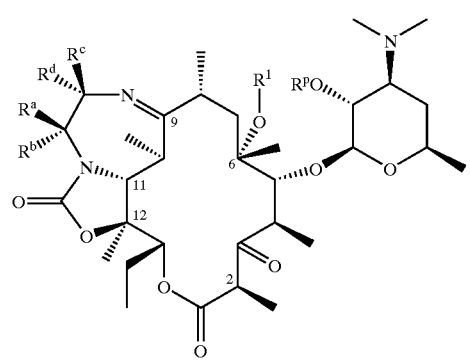

wherein Y, $R^1$, $R^a$, $R^b$, $R^c$, $R^d$ and $R^p$ are as previously defined, with a suitable electrophilic reagent in the presence of base to obtain a compound of the formula:

(IX)

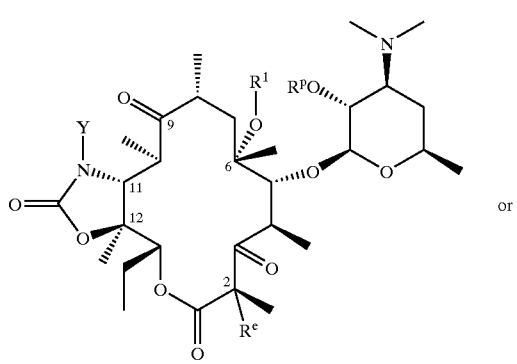

or (X)

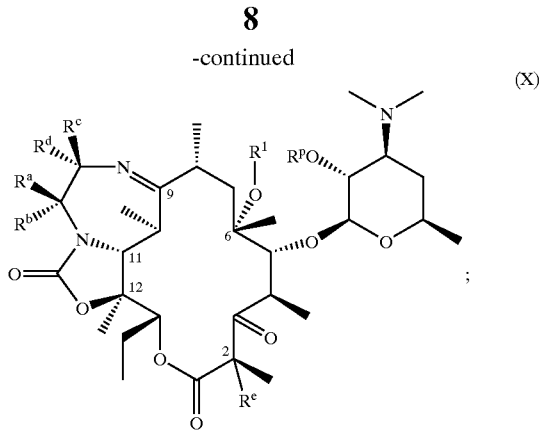

wherein Re is a C2-leaving group selected from the group consisting of hydroxy, halide, sulfone, sulfoxide, sulfide and selenide;

(b) oxidizing the C2-position of a compound in step (a), as necessary, and eliminating the C2-leaving group optionally in the presence of a base to provide a suitable C2-exocyclic methylene group;

(c) derivatizing the C2-position in one of the following manners:

(i) oxidizing the C2-exocylic methylene of the compound obtained in step (b) followed by reacting with a carbon, nitrogen, sulfur, or oxygen nucleophile;

(ii) treating the compound obtained in step (b) with a carbon, nitrogen, sulfur or oxygen nucleophile; and (iii) hydrolyzing the compound obtained in step (b) under basic conditions followed by alkylation, oxidation or halogenation; and (d) optionally removing any hydroxy protecting group that may be present.

In yet another aspect, the invention relates to a pharmaceutical composition comprising a compound as described above and a pharmaceutically acceptable carrier.

Yet another aspect of the invention relates to a method of treating a bacterial infection comprising administering a therapeutically effective amount of a compound of the invention to a patient in need of such treatment.

DETAILED DESCRIPTION OF THE INVENTION

Definitions

The term "$C_1$–$C_6$ alkyl" as used herein refers to saturated, straight, or branched chain hydrocarbon radicals derived from a hydrocarbon moiety containing between one and six carbon atoms by removal of a single hydrogen atom. In general, a group denoted as $C_x$–$C_y$, wherein x and y are integers, refers to a group of x to y carbon atoms. For example, the group $C_x$–$C_y$ alkyl, wherein x is 1 and y is 3, includes $C_1$–$C_3$ alkyl radicals such as methyl, ethyl, propyl, and isopropyl. Exemplary $C_1$–$C_6$ alkyl radicals include methyl, ethyl, propyl, isopropyl, n-butyl, tert-butyl, neopentyl, and n-hexyl. Examples of $C_1$–$C_{12}$ alkyl radicals include all the foregoing examples, as well as n-heptyl, n-octyl, n-nonyl, n-decyl, n-undecyl, and n-docecyl.

The term "$C_1$–$C_6$ alkenyl" as used herein refers to straight- or branched-chain hydrocarbon radicals comprising one to six carbon atoms, respectively, which contain one or more carbon—carbon double bonds. Compounds of the invention have either a known configuration or exist as a mixture of isomers.

The term "$C_1$–$C_6$ alkynyl" used herein refers to straight- or branched-chain hydrocarbon radicals comprising one to six carbon atoms, respectively, which contain one or more carbon—carbon triple bonds. Compounds of the invention have either a known configuration or exist as a mixture of isomers.

The term "aryl" as used herein refers to a mono-, fused bicyclic or fused tricyclic carbocyclic ring system having one or more aromatic rings including, but not limited to, phenyl, naphthyl, indanyl, indenyl, tetrahydronaphthyl, anthracenyl, phenanthrenyl, biphenylenyl, fluorenyl, and the like.

The term "substituted aryl" as used herein refers to an aryl group as defined herein substituted by independent replacement of one, two or three of the hydrogen atoms thereon with Cl, Br, F, I, OH, CN, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group. Substituents also include alkenyloxy, for example, methylenedioxy and ethylenedioxy. The substituted aryl groups also include tetrafluorophenyl and pentafluorophenyl.

The terms "halo", "halide", and "halogen" as used herein refer to an atom selected from fluorine, chlorine, bromine, and iodine.

The term "heteroaryl" as used herein refers to a cyclic aromatic radical having from five to ten ring atoms of which one ring atom is selected from S, O and N; one, two, or three ring atoms may be additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, tetrazolyl, thiophenyl, furanyl, quinolinyl, quinoxalinyl, isoquinolinyl, and the like.

The term "heterocyclic", "heterocycle", and "heterocycloalkyl" as used herein refers to a non-aromatic partially unsaturated or fully saturated 3- to 10-membered ring system which includes single rings of 3 to 8 atoms in size and bi- or tricyclic ring systems which may include aromatic six-membered aryl or heteroaryl rings fused to a non-aromatic ring. These heterocyclic rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heteroaryl" as used herein refers to a heteroaryl group as defined above substituted by independent replacement of one, two or three of the hydrogen atoms thereon with Cl, Br, F, I, OH, cyano, $C_1$–$C_3$ alkyl, $C_1$–$C_6$ alkoxy, $C_1$–$C_6$ alkoxy substituted with aryl, haloalkyl, thioalkoxy, alkoxy, alkoxyalkoxy, amino, alkylamino, dialkylamino, mercapto, —$SO_3H$, nitro, carboxaldehyde, carboxy, alkoxycarbonyl and carboxamide. In addition, any one substitutent may be an aryl, arylalkyl, cycloalkyl, heteroaryl, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, cyano, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

The term "hydroxy protecting group" as used herein refers to an easily removable group to which are known in the art to protect a hydroxyl group against undesirable reaction during synthetic procedures and to be selectively removable. The use of hydroxy protecting groups is well known in the art for protecting groups against undesirable reactions during a synthetic procedure and many such protecting groups are known, c.f., for example T. H. Wiley & Sons, New York (1991). Examplary hydroxy protecting groups are methylthiomethyl, tert-dimethylsilyl, tert-butyldiphenylsilyl, acyl substituted with an aromatic group, and the like.

The term "protected hydroxy" as used herein refers to a hydroxy group protected with a hydroxy protecting group as defined above including, but not limited to, benzoyl, acetyl, trimethylsilyl, triethylsilyl, methoxymethyl, and the like.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences*, 66: 1–19 (1977), which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable solvate" represents an aggregate that comprises one to three molecules of the solute, such as a compound of the invention, with one, two, or three molecules of solvent. Suitable pharmaceutically acceptable solvates include hydrates, wherein the solute is one, two or three molecules of water, and those solvates wherein the solute is a solvent which is suitable for use in a pharmaceutical product, such as ethanol.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Numerous asymmetric centers may exist in the compounds of the present invention. Except where otherwise noted, the present invention contemplates the various stereoisomers and mixtures thereof.

A preferred compound of the invention is represented by the formula:

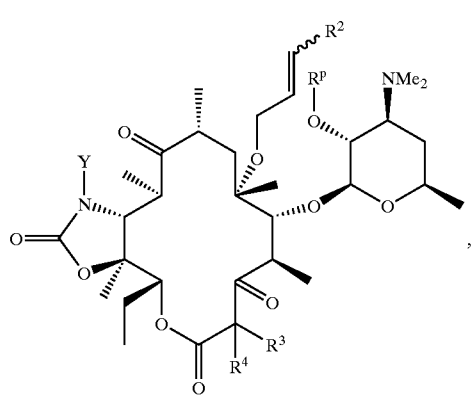

(XI)

wherein Y, $R^2$, $R^3$, $R^4$, and $R^p$ are as previously defined.

Another preferred compound of the invention is represented by the formula:

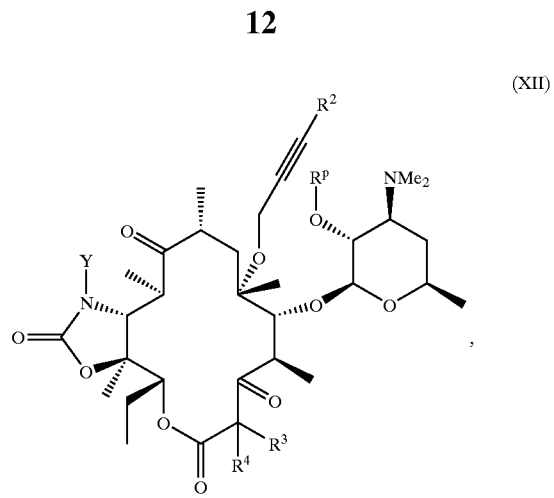

(XII)

wherein Y, $R^2$, $R^3$, $R^4$ and $R^p$ are as previously defined.

Yet another preferred compound of the invention is represented by the formula:

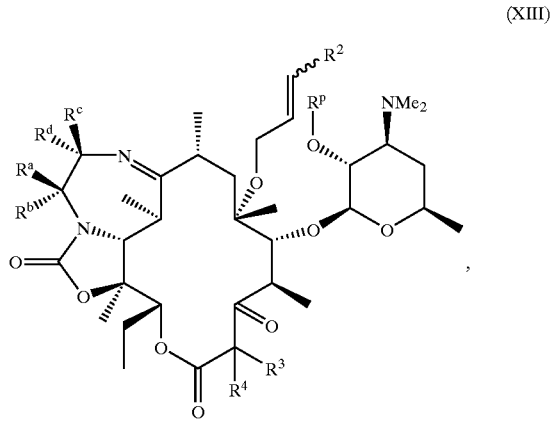

(XIII)

wherein $R^2$, $R^3$, $R^4$, $R^a$, $R^b$, $R^c$, $R^d$, and $R^p$, are as previously defined.

Still yet another preferred compound of the invention is represented by the formula:

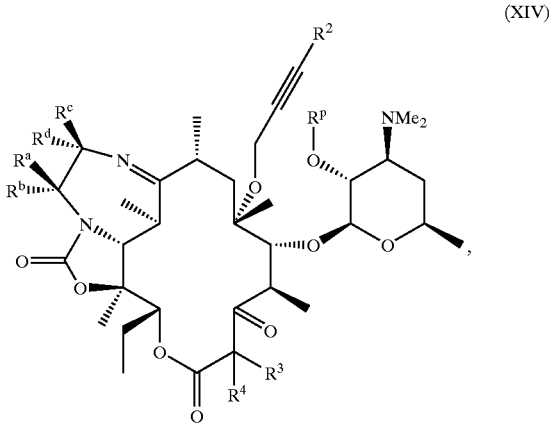

(XIV)

wherein $R^2$, $R^3$, $R^4$, $R^a$, $R^b$, $R^c$, $R^d$, and $R^p$, are as previously defined.

Representative compounds of the invention include, but are not limited to the following:

Compound of formula (XI), $R^p$ is benzoyl, Y is Hydrogen, $R^2$ is 3-quinolyl, $R^3$ and $R^4$ taken together is =$CH_2$;

Compound of formula (XI), $R^p$ is hydrogen, Y is Hydrogen, $R^2$ is 3-quinolyl, $R^3$ is hydrogen and $R^4$ is hydrogen;

Compound of formula (I), $R^p$ is hydrogen, Y is hydrogen, $R^1$ is —$CH_2CH(OH)CH(OH)$—(3-quinolyl), $R^3$ is —$CH_2OH$ and $R^4$ is OH;

Compound of formula (I), $R^p$ is hydrogen, Y is hydrogen, $R^1$ is —$CH_2CH$=O, $R^3$ is —$CH_2OH$ and $R^4$ is OH;

Compound of formula (XI), $R^p$ is hydrogen, Y is Hydrogen, $R^2$ is 3-quinolyl, $R^3$ is —$CH_2CH$=$CH_2$ and $R^4$ is hydrogen;

Compound of formula (XI), $R^p$ is hydrogen, Y is Hydrogen, $R^2$ is 3-quinolyl, $R^3$ is —$CH_2SO_3H$ and $R^4$ is hydrogen;

Compound of formula (XI), $R^p$ is hydrogen, Y is Hydrogen, $R^2$ is 3-quinolyl, $R^3$ is —$CH_2CH(CO_2Me)_2$ and $R^4$ is hydrogen;

Compound of formula (XI), $R^p$ is hydrogen, Y is Hydrogen, $R^2$ is 3-quinolyl, $R^3$ and $R^4$ taken together is —$CH_2O$—;

Compound of formula (XI), $R^p$ is hydrogen, Y is Hydrogen, $R^2$ is 3-quinolyl, $R^3$ is F and $R^4$ is hydrogen;

Compound of formula (XI), $R^p$ is hydrogen, Y is Hydrogen, $R^2$ is 3-quinolyl, $R^3$ is F and $R^4$ is F;

Compound of formula (XI), $R^p$ is hydrogen, Y is Hydrogen, $R^2$ is 3-quinolyl, $R^3$ is —$CH_2F$ and R is F;

Compound of formula (XI), $R^p$ is hydrogen, Y is hydrogen, $R^2$ is hydrogen, $R^3$ is hydrogen and $R^4$ is hydrogen;

Compound of formula (XII), $R^p$ is hydrogen, Y is hydrogen, $R^2$ is hydrogen, $R^3$ is hydroxy and $R^4$ is hydrogen;

Compound of formula (XII), $R^p$ is hydrogen, Y is hydrogen, $R^2$ is hydrogen, $R^3$ is hydrogen and $R^4$ is hydrogen;

Compound of formula (XIII), $R^p$ is hydrogen, $R^2$ is hydrogen, $R^3$ is hydrogen, $R^4$ is hydrogen, $R^a$ is hydrogen, $R^b$ is hydrogen, $R^c$ is hydrogen and $R^d$ is hydrogen;

Compound of formula (XIV), $R^p$ is hydrogen, $R^2$ is hydrogen, $R^3$ is hydrogen, $R^4$ is hydrogen, $R^a$ is hydrogen, $R^b$ is hydrogen, $R^c$ is hydrogen and $R^d$ is hydrogen;

Compound of formula (XII), $R^p$ is hydrogen, Y is Hydrogen, $R^2$ is 3-quinolyl, $R^3$ is hydrogen and $R^4$ is hydrogen;

Compound of formula (XIII), $R^p$ is Hydrogen, $R^2$ is 3-quinolyl, $R^3$ is hydrogen, $R^4$ is hydrogen, $R^a$ is hydrogen, $R^b$ is hydrogen, $R^c$ is hydrogen and $R^d$ is hydrogen;

Compound of formula (XIV), $R^p$ is Hydrogen, $R^2$ is 3-quinolyl, $R^3$ is hydrogen, $R^4$ is hydrogen, $R^a$ is hydrogen, $R^b$ is hydrogen, $R^c$ is hydrogen and R is hydrogen;

Compound of formula (XI), $R^p$ is hydrogen, Y is hydrogen, $R^2$ is hydrogen, $R^3$ is F and $R^4$ is hydrogen;

Compound of formula (XII), $R^p$ is hydrogen, Y is hydrogen, $R^2$ is hydrogen, $R^3$ is F and $R^4$ is hydrogen;

Compound of formula (XIII), $R^p$ is hydrogen, $R^2$ is hydrogen, $R^3$ is F, $R^4$ is hydrogen, $R^a$ is hydrogen, $R^b$ is hydrogen, $R^c$ is hydrogen and $R^d$ is hydrogen;

Compound of formula (XIV), $R^p$ is hydrogen, $R^2$ is hydrogen, $R^3$ is F, $R^4$ is hydrogen, $R^a$ is hydrogen, $R^b$ is hydrogen, $R^c$ is hydrogen and $R^d$ is hydrogen;

Compound of formula (XI), $R^p$ is hydrogen, Y is hydrogen, $R^2$ is hydrogen, $R^3$ is F and $R^4$ is F;

Compound of formula (XII), $R^p$ is hydrogen, Y is hydrogen, $R^2$ is hydrogen, $R^3$ is F and $R^4$ is F;

Compound of formula (XIII), $R^p$ is hydrogen, $R^2$ is hydrogen, $R^3$ is F, R is F, $R^a$ is hydrogen, $R^b$ is hydrogen, $R^c$ is hydrogen, and $R^d$ is hydrogen;

Compound of formula (XIV), $R^p$ is hydrogen, $R^2$ is hydrogen, $R^3$ is F, $R^4$ is F, $R^a$ is hydrogen, $R^b$ is hydrogen, $R^c$ is hydrogen, and $R^d$ is hydrogen;

Compound of formula (XI), $R^p$ is hydrogen, Y is hydrogen, $R^2$ is 8-quinoxaline, $R^3$ is F and $R^4$ is hydrogen;

Compound of formula (XII), $R^p$ is hydrogen, Y is Hydrogen, $R^2$ is 3-quinolyl, $R^3$ is F and $R^4$ is hydrogen;

Compound of formula (XIII), $R^p$ is Hydrogen, $R^2$ is 3-quinolyl, $R^3$ is F, $R^4$ is hydrogen, $R^a$ is hydrogen, $R^b$ is hydrogen, $R^c$ is hydrogen, and $R^d$ is hydrogen;

Compound of formula (XIV), $R^p$ is Hydrogen, $R^2$ is 3-quinolyl, $R^3$ is F, $R^4$ is hydrogen, $R^a$ is hydrogen, $R^b$ is hydrogen, $R^c$ is hydrogen, and $R^d$ is hydrogen;

Compound of formula (XI), $R^p$ is hydrogen, Y is hydrogen, $R^2$ is 8-quinoxaline, $R^3$ is F and $R^4$ is F;

Compound of formula (XII), $R^p$ is hydrogen, Y is Hydrogen, $R^2$ is 3-quinolyl, $R^3$ is F and $R^4$ is F;

Compound of formula (XIII), $R^p$ is Hydrogen, $R^2$ is 3-quinolyl, $R^3$ is F, $R^4$ is F, $R^a$ is hydrogen, $R^b$ is hydrogen, $R^c$ is hydrogen, and $R^d$ is hydrogen;

Compound of formula (XIV), $R^p$ is Hydrogen, $R^2$ is 3-quinolyl, $R^3$ is F, $R^4$ is F, $R^a$ is hydrogen, $R^b$ is hydrogen, $R^c$ is hydrogen, and $R^d$ is hydrogen;

Compound of formula (I), $R^p$ is hydrogen, Y is hydrogen, $R^1$ is methyl, $R^3$ is hydrogen and $R^4$ is hydrogen;

Compound of formula (II), $R^p$ is hydrogen, $R^1$ is methyl, $R^3$ is hydrogen, $R^4$ is hydrogen, $R^a$ is hydrogen, $R^b$ is hydrogen, $R^c$ is hydrogen, and $R^d$ is hydrogen;

Compound of formula (I), $R^p$ is hydrogen, Y is hydrogen, $R^1$ is methyl, $R^3$ is —$CH_2C$=$CH_2$ and $R^4$ is hydrogen;

Compound of formula (I), $R^p$ is hydrogen, Y is hydrogen, $R^1$ is methyl, $R^3$ is —$CH_2C$≡$CH$ and $R^4$ is hydrogen;

Compound of formula (II), $R^p$ is hydrogen, $R^1$ is methyl, $R^3$ is —$CH_2C$=$CH_2$, $R^4$ is hydrogen, $R^a$ is hydrogen, $R^b$ is hydrogen, $R^c$ is hydrogen, and $R^d$ is hydrogen;

Compound of formula (II), $R^p$ is hydrogen, $R^1$ is methyl, $R^3$ is —$CH_2C$≡$CH$, $R^4$ is hydrogen, $R^a$ is hydrogen, $R^b$ is hydrogen, $R^c$ is hydrogen, and $R^d$ is hydrogen;

Compound of formula (II), $R^p$ is hydrogen, Y is hydrogen, $R^1$ is methyl, $R^3$ is —$CH_2C$=$CH$—(3-quinolyl) and $R^4$ is hydrogen;

Compound of formula (I), $R^p$ is hydrogen, Y is hydrogen, $R^1$ is methyl, $R^3$ is —$CH_2C$≡$C$—(3-quinolyl) and $R^4$ is hydrogen;

Compound of formula (II), $R^p$ is hydrogen, $R^1$ is methyl, $R^3$ is —$CH_2C$=$CH$—(3-quinolyl), $R^4$ is hydrogen, $R^a$ is hydrogen, $R^b$ is hydrogen, $R^c$ is hydrogen, and $R^d$ is hydrogen;

Compound of formula (II), $R^p$ is hydrogen, $R^1$ is methyl, $R^3$ is —$CH_2C$≡$C$—(3-quinolyl), $R^4$ is hydrogen, $R^a$ is hydrogen, $R^b$ is hydrogen, $R^c$ is hydrogen, and $R^d$ is hydrogen;

Compound of formula (I), $R^p$ is hydrogen, Y is hydrogen, $R^1$ is methyl, $R^3$ is —$CH_2C$=$CH_2$ and $R^4$ is F;

Compound of formula (I), $R^p$ is hydrogen, Y is hydrogen, $R^1$ is methyl, $R^3$ is —$CH_2C$≡CH and $R^4$ is F;

Compound of formula (II), $R^p$ is hydrogen, $R^1$ is methyl, $R^3$ is —$CH_2C$=$CH_2$, $R^4$ is F, $R^a$ is hydrogen, $R^b$ is hydrogen, $R^c$ is hydrogen and $R^d$ is hydrogen;

Compound of formula (II), $R^p$ is hydrogen, $R^1$ is methyl, $R^3$ is —$CH_2C$≡CH, $R^4$ is hydrogen, $R^a$ is hydrogen, $R^b$ is hydrogen, $R^c$ is hydrogen and $R^d$ is hydrogen;

Compound of formula (I), $R^p$ is hydrogen, Y is hydrogen, $R^1$ is methyl, $R^3$ is —$CH_2C$=CH—(3-quinolyl), and $R^4$ is F;

Compound of formula (I), $R^p$ is hydrogen, Y is hydrogen, $R^1$ is methyl, $R^3$ is —$CH_2C$≡C—(3-quinolyl), and $R^4$ is F;

Compound of formula (II), $R^p$ is hydrogen, $R^1$ is methyl, $R^3$ is —$CH_2C$=CH—(3-quinolyl), $R^4$ is F, $R^a$ is hydrogen, $R^c$ is hydrogen, $R^c$ is hydrogen and $R^d$ is hydrogen; and Compound of formula (II), $R^p$ is hydrogen, $R^1$ is methyl, $R^3$ is —$CH_2C$≡C—(3-quinolyl), $R^4$ is F, Ra is hydrogen, Kb is hydrogen, $R^c$ is hydrogen and $R^d$ is hydrogen.

The representative compounds can be prepared from a method as previously described, allowing for minor modification of the reagents and conditions to obtain a desired compound named above. A compound of the invention can be isolated and purified by methods known in the art and provide suitable compounds for a composition of the invention.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation and ear drops are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants, such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more, such as from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of a compounds of the invention per day in a single or multiple doses.

Abbreviations

Abbreviations which have been used in the descriptions of the scheme and the examples that follow are: $^t$BuOH for t-butyl alcohol; CDI for carbonyldiimidazole; CuBr.DMS for copper(I) bromide-dimethylsulfide complex; m-CPBA for m-chloroperbenzoic acid, DBU for 1,8-diazabicyclo[5.4.0]undec-7-ene; DMSO for dimethyl sulfoxide; EtOAc for ethyl acetate; DMF for dimethylformamide; KO$^t$Bu for potassium t-butoxide; MeOH for methanol; NaH for sodium hydride; NCS for N-chlorosuccinimide; NMO for N-methylmorpholine-N-oxide; Me$_2$S for dimethyl sulfide; Ph for phenyl; Pd(PPh$_3$)$_2$Cl$_2$ for dipalladium (triphenylphosphine) dichloride; PhSeCl for phenylselenyl chloride; (PhSO$_2$)$_2$NF for N-fluorobenzenesulfonimide; TEA for triethylamine; THF for tetrahydrofuran; and TPP for triphenylphosphine. Starting materials, reagents, and solvents are available from Aldrich Chemical Company (Milwaukee, Wiss.) unless otherwise noted herein.

Synthetic Methods

The compounds and processes of the present invention will be better understood in connection with the following synthetic Schemes, which illustrate the methods by which the compounds of the invention may be prepared. The compounds of general formula (I) and (II) may be prepared by derivatizing a 2-nor-6—O-substituted ketolide compound or derivative thereof prepared from a 2-nor erythromycin fermentation product or, alternatively, by chemically modifying the C2-position of a suitable 6—O-substituted ketolide obtained from erythromycin A or a derivative thereof.

A 2-nor-6—O-ketolide substrate can be prepared from a 2-norerythromycin A (available from Abbott Laboratories, Abbott Park, Ill.), which is obtained by fermentation techniques. The 2-nor derivatives of erythromycin A, B, C and D were produced in a strain *Streptomyces erythreus* 12693-240 (NRRL B-1 8053) transformed by pNHI bearing DNA (NRRL B-1 8054) from *Streptomyces antibioticus*. Macrolide 2-norerythromycin compounds have been identified from the fermentation medium of *S. erythreus* 12693-240. A subculture of this microorganism was deposited in the permanent collection of the National Center for Agricultural Utilization Research, United States Department of Agriculture, 1815 North University Street, Peoria, Ill. 61604, U.S.A., and accorded accession number NRRL B-18055.

To obtain the 2-norerythromycin compounds, *Streptomyces erythreus* strain NRRL 12693-240 was innoculated into 500 ml of SCM medium (1.5% soluble starch, thiostrepton at 2 $\mu$g/ml) and grown for 3–6 days at 32° C. The entire culture was then innoculated into 10 liters of fresh SCM medium containing thiostrepton at 2 $\mu$g/ml and 5% soy bean oil and fermented for a period of 7 days at 32° C. The fermentation medium was sequentially extracted with ethyl acetate to obtain the antibiotic-containing fractions. Methods for preparing 2-norerythromycin A, B, C or D are described in U.S. Pat. No. 4,874,748, the disclosure of which is incorporated herein.

The 2-norerythromycin compounds can be treated in accordance with reaction conditions for the protection, oximation, alkylation, deprotection, deoximation, removal of the cladinose sugar (descladinozation), oxidation and acylation reactions described in the art to obtain a 10,11-anhydro-12-acylimidazolyl erythromycin A derivative, which can be transformed into a suitable substrate for C2-derivatization. In a preferred process, an 11,12-carbamate derivative or a tricyclic imine derivative is prepared from the 10,11-anhydro-12-acylimidazolyl ketolide intermediate. An example of a procedure suitable for preparing the 6—O-substituted ketolide substrate is shown below in Scheme 1.

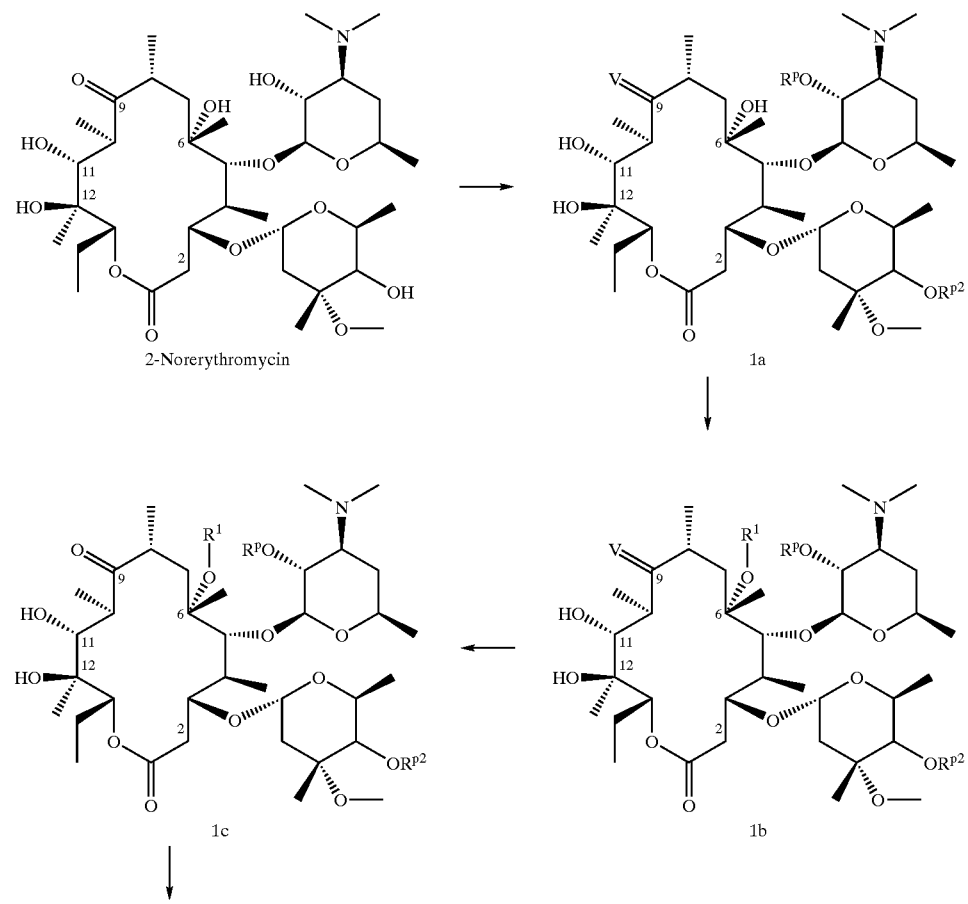

-continued
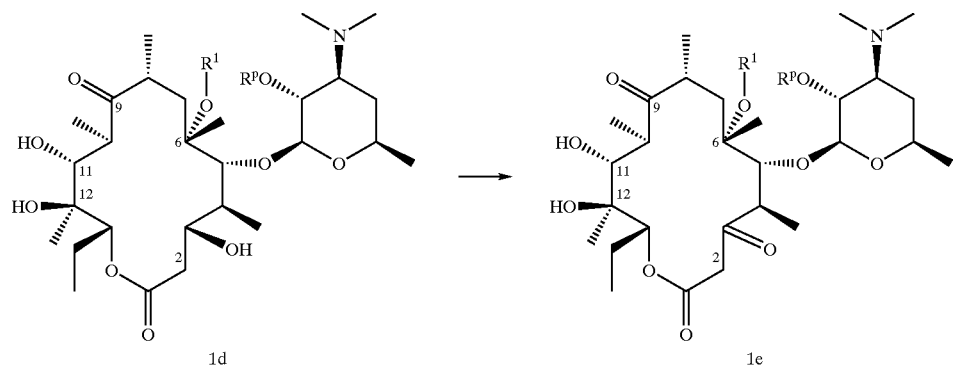
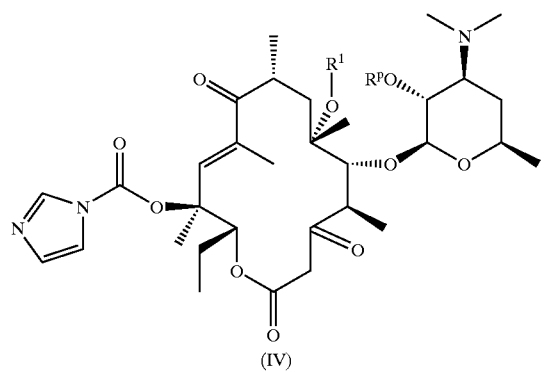
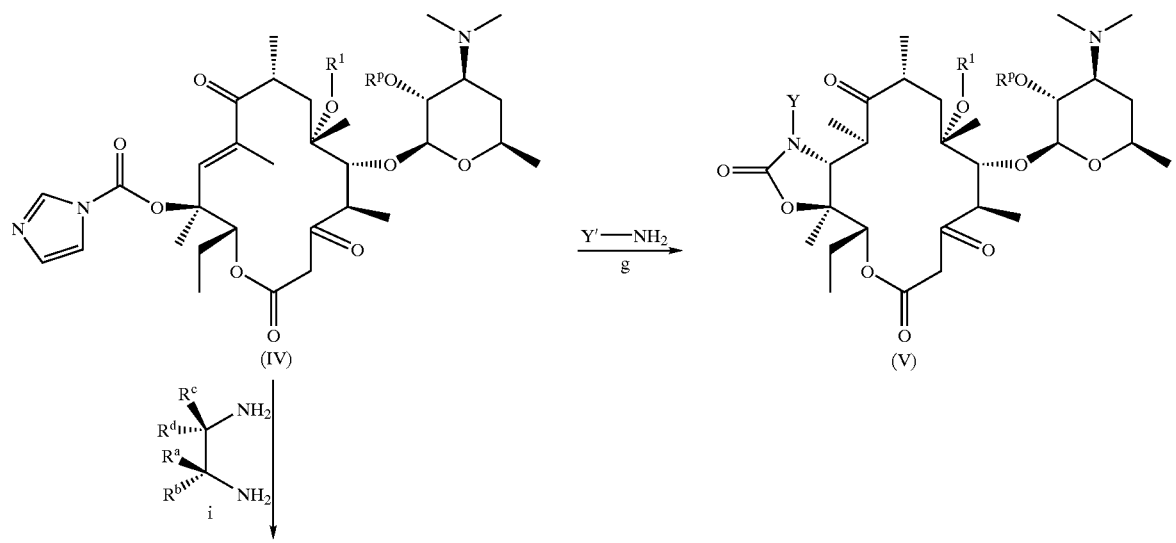

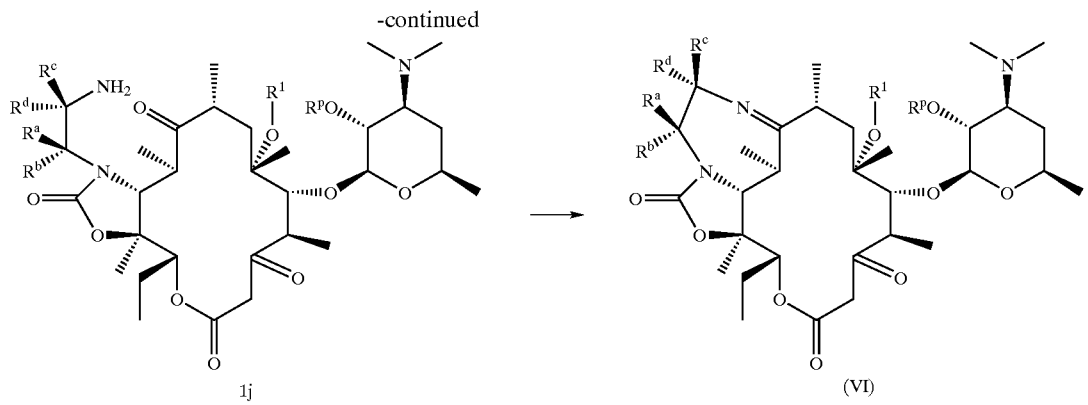

As shown in Scheme 1, conversion of 2-norerythroycin A to a compound 1a can be carried out using methods for converting a 9-oxime erythromycin derivative. The C9-carbonyl group of the 2-norerythromycin A is typically protected as an oxime, wherein V is N—O—$(CH_2)_s$—$R^x$, N—O—C(O)—$(CH_2)_s$—$R^x$, or N—O—$C(R^y)(R^z)$-O—$(CH_2)_s$—$R^x$, wherein s is 0 to 5 and Rx is (a) hydrogen, (b) alkyl (c) substituted alkyl (d) aryl, (e) substituted aryl, (f) heteroaryl, and (g) substituted heteroaryl, and wherein $R^y$ and $R^z$ are independently selected from (a) hydrogen, (b) unsubstituted $C_1$–$C_{12}$-alkyl, (c) $C_1$–$C_{12}$-alkyl substituted with aryl, and (d) $C_1$–$C_{12}$-alkyl substituted with substituted aryl, or $R^y$ and $R^z$ taken together with the carbon to which they are attached form a $C_3$–$C_{12}$-cycloalkyl ring. A preferred protected oxime group V is N—O—(1-isopropoxycyclohexyl) or N—O—C(O)-phenyl (i.e. N—O-benzoyl). Conditions for the protection of the 9-oxime of erythromycin derivatives are further described in U.S. Pat. Nos. 4,990,602; 4,331,803, 4,680,368; and 4,670,549; and European Patent Application EP 260,938, the disclosures of which are herein incorporated by reference.

The 2'- and optionally the 4"-hydroxy groups of the erythromycin A can be treated with a suitable hydroxy protecting reagent in an aprotic solvent. Hydroxy protecting reagents include, for example, acetic anhydride, benzoic anhydride, hexamethyldisilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran, N-methyl pyrrolidinone or a mixture thereof. The protection of the 2'- and optionally the 4"-hydroxy groups of the C9-protected erythromycin A may be accomplished sequentially or simultaneously. The variables $R^p$ and $Rp^2$ denote hydrogen or a hydroxy protecting group when used throughout the specification in the structural formulas. Preferred protecting groups include, but are not limited to, acetyl, trimethylsilyl, and benzoyl. A thorough discussion of protecting groups and the solvents in which they are most effective is provided by T. W. Greene and P. G. M. Wuts in *Protective Groups in Organic Synthesis,* 2nd ed., John Wiley & Son, Inc., 1991.

Alkylation of the 6—O-hydroxy group of 1a can be accomplished with an alkylating agent in the presence of base to obtain 1b. Suitable alkylating agents include alkyl chlorides, bromides, iodides or alkyl sulfonates. Specific examples of other alkylating agents are allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 1-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, and 1,3-dibromo-1-propene. Examples of alkyl sulfonates are allyl tosylate, 3-phenylpropyl trifluoromethane sulfonate, and n-butylmethanesulfonate. Examples of the solvents used are aprotic solvents such as DMSO, diethylsulfoxide, N,N-dimethylformamide, NN-dimethylacetamide, N-methyl-2-pyrrolidone, hexamethylphosphoric triamide, mixtures thereof or mixtures of one of these solvents with ether, tetrahydrofuran, 1,2-dimethoxyethane, acetonitrile, ethyl acetate, or acetone. Examples of the base which can be used are potassium hydroxide, cesium hydroxide, tetraalkylammonium hydroxide, sodium hydride, potassium hydride, and alkali metal alkoxides such as potassium isopropoxide, potassium tert-butoxide, and potassium iso-butoxide. An especially preferred method of carrying out the alkylation is treatment of 1a with allyl bromide or propargyl bromide in a DMSO/THF mixture with potassium hydroxide or potassium t-butoxide as the base.

Deprotection of the C9-oxime of 1b, wherein V is a protected oxime, can be accomplished under neutral, acidic or basic conditions. Exemplary conditions for deprotecting a protected oxime of the formula N—O—C(O)—$(CH_2)_s$—$R^x$ include, but are not limited to, treatment with an alcoholic solvent at room temperature or at reflux. Preferably, the 9-oxime is deprotected in this manner when $R^p$ is an ester, such as acetate or benzoate. Alcoholic solvents preferred for the deprotection are methanol or ethanol. Exemplary conditions for converting the protected oxime N—O—$C(R^y)(R^z)$—O—$R^x$, wherein $R^x$, $R^y$, and $R^z$ are as previously described, to the oxime (N—OH) involve treating compound 1b with aqueous acid in acetonitrile. Aqueous acids suitable for the reaction include, but are not limited to, aqueous acetic acid, hydrochloric acid, and sulfuric acid. During the deprotection of the oxime, the 2'- and 4"-hydroxy protecting groups ($R^p$ and $R^{p2}$) can be removed in the process. A thorough discussion of the procedures, reagents and conditions for removing protecting groups is discussed by T. W. Greene and P. G. M. Wuts in *Protective Groups in Organic Synthesis,* 3rd ed., John Wiley & Son, Inc., (1991), which is herein incorporated by reference.

The deoximation reaction can be carried out by reacting the deprotected C9-oxime of 1b, with an inorganic sulfur oxide or an inorganic nitrite salt in a protic solvent. Exemplary inorganic sulfur oxide compounds are sodium hydrogen sulfite, sodium thiosulfate, sodium sulfite, sodium metabisulfite, sodium dithionate, potassium thiosulfate, potassium metabisulfite, and the like. Suitable inorganic nitrite salts include, for example, sodium nitrite or potassium nitrite, and the like. Examples of the solvents used are protic solvents such as water, methanol, ethanol, propanol, isopropanol, trimethylsilanol, or a mixture of one or more of the mentioned solvents, and the like. The reaction is optionally carried out in the presence of an organic acid, such as formic acid, acetic acid and trifluoroacetic acid. Hydrochloric acid is also suitable for the reaction. The amount of acid used is from about 1 to about 10 equivalents of the amount of compound 1b. In a preferred embodiment, the reaction of compound 1b is carried out using sodium nitrite and HCl in ethanol and water to give compound 1c.

The cladinose moiety of compound 1c is removed by mild aqueous acid hydrolysis to give 1d. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably $-10°$ C. to $70°$ C.

The 2'-hydroxy group of the macrolide is optionally protected as previously described using a hydroxy protecting reagent in an aprotic solvent. Preferred hydroxy protecting reagents are acetic anhydride, benzoyl anhydride, or trialkylsilyl chloride. Preferably, the aprotic solvent is dichloromethane, chloroform, DMF, tetrahydrofuran (THF), N-methyl pyrrolidinone or a mixture thereof. A particularly preferred protecting group for the 2'-position (RP) is acetate or benzoate. Protection of the hydroxy group can be accomplished before or after the descladinozation reaction.

The 3-hydroxy group of 1d is oxidized to the ketone 1e using a modified Swern oxidation procedure or Corey-Kim oxidation conditions. Suitable oxidizing agents are N-chloro-succinimide-dimethyl sulfide or carbodiimide-dimethylsulfoxide. In a typical example, 1d is added into a pre-formed N-chlorosuccinimide and dimethyl sulfide complex in a chlorinated solvent, such as methylene chloride, at $-20$ to $25°$ C. After stirring for 0.5–4 hours, a tertiary amine, such as triethylamine or diisopropylethylamine (Hunig's base), is added to produce the corresponding ketone.

The 11,12-diol group of 1e can be further treated to obtain an 10,11-anhydro-12-imidazolyl intermediate compound (IV), which can be converted into an 11,12-carbamate of formula (V) or the tricyclic imine (VI). The intermediate compound of formula (IV) may be prepared from compound 1e by treatment of the latter under anhydrous conditions with an alkali metal hydride or bis(trimethylsilyl) amide in the presence of carbonyldiimidazole in an aprotic solvent. Suitable aprotic solvents are those previously defined. Exemplary reagents can be sodium hydride, lithium hydride, sodium hexamethyldisilazide, lithium hexamethyldisilazide, and the like. Preferably, the solvent is tetrahydrofuran, dimethylformamide, or a mixture thereof. The reaction may require cooling or heating, depending upon the conditions used. The reaction temperature may be from $-20°$ C. to $70°$ C., and preferably from $0°$ C. to room temperature. The reaction may require 0.5 hours to 10 days, and is preferably accomplished in 1 to 5 days.

Alternatively, compound 1e is treated with an alkali metal hydride and a phosgene reagent under anhydrous conditions, followed by a base catalyzed decarboxylation, or can be treated with methanesulfonic anhydride in pyridine, followed by treatment with an amine base to provide a suitable anhydro intermediate for treatment with the alkali metal hydride base and carbonyldiimidazole to give compound (IV) in a stepwise manner. Preferably, the phosgene reagent is phosgene, diphosgene, or triphosgene.

To obtain compounds of formula (V), wherein Y is as previously defined, compound (IV) is reacted with a primary amine g of the formula $Y'$—$NH_2$, wherein $Y'$ is $Z$—$R^7$ and Z and $R^7$ are as previously defined. The reaction is carried out in a suitable solvent from room temperature to reflux temperature for about 1 to about 10 days. Exemplary solvents are acetonitrile, tetrahydrofuran, dimethyl formamide, dimethylsulfoxide, dimethyl ether, N-methyl pyrrolidinone, water, or a mixture thereof. Preferred solvents are aqueous acetonitrile, and aqueous DMF.

The compound of formula (V), wherein Y corresponds to hydrogen, can be prepared by reacting a compound of formula (IV) with aqueous ammonia hydroxide or anhydrous ammonia, preferably in acetonitrile, under the conditions as described above for the primary amine.

The prepared 11,12-carbamate derivatives are optionally deprotected. When the protecting group is an ester, the protecting group may be removed by treatment with an organic alcohol, such as methanol or ethanol. Exemplary esters which can be deprotected by treating the ketolide derivatives with an organic alcohol are acetate, benzoate, and the like. When the protecting group is a trialkylsilyl group, deprotection by treatment with fluoride in a polar organic solvent, such as THF or acetonitrile, or aqueous acid hydrolysis is preferred.

Compound (IV) can be reacted with a diamine compound i, wherein $R^a$, $R^b$, $R^c$ and $R^d$ are as previously defined, in a suitable polar organic solvent to obtain a corresponding bicyclic amine compound 1j. The diamines for the synthesis can be purchased or prepared by means well known in the art. The compounds have the substituents $R^a$, $R^b$, $R^c$ and $R^d$ in accordance with the desired substituents and chirality of the starting material.

Exemplary solvents for the reaction are selected from the group consisting of aqueous acetonitrile, DMF, aqueous DMF, and the like. One amino group of the diamine reagent can be optionally protected to differentiate the two diamine and deprotected prior to cyclization.

Cyclization of the bicyclic amine 1j by treatment with dilute acid in a suitable organic solvent affords the tricyclic derivatives of the invention. The reaction can be accomplished in a period of from about 1 to 10 days at temperatures from about room temperature to reflux. Exemplary acids are acetic acid or HCl. A suitable organic solvent is an alcoholic solvent, such as methanol, ethanol, propanol, and the like, or non polar solvent, such as benzene or toluene.

Optional deprotection of the compound obtained therefrom affords a tricyclic ketolide derivative (VI).

The 2-position of (V) or (VI) can be optionally derivatized to obtain a 2-nor-2-substituted 6—O-alkyl ketolide derivative.

C-2 Modification of 6—O-Alkyl Ketolide Derivatives of Erythromycin

In another method, a 6-O-alkylated ketolide substrate can be prepared from erythromycin A (available from Abbott Laboratories, Abbott Park, Ill.), in accordance with methods readily available to one of skill in the art and the C2-position can be suitably modified to provide a 2-nor-6-O-alkylated ketolide substrate, which can be further derivatized.

Erythromycin A can be treated in accordance with the reaction conditions previously described for the protection, deprotection, alkylation, deoximation, removal of the cladinose sugar (descladinozation), oxidation, and acylation reactions of the 2-norerythromycin A substrate. Exemplary techniques for preparing the 6—O-substituted ketolide are disclosed in U.S. Pat. No. 5,866,549 and PCT Publication No. WO 99/21871, which are herein incorporated by reference. An example of a method for obtaining a 6-O-alkylated ketolide is described in Scheme 2.

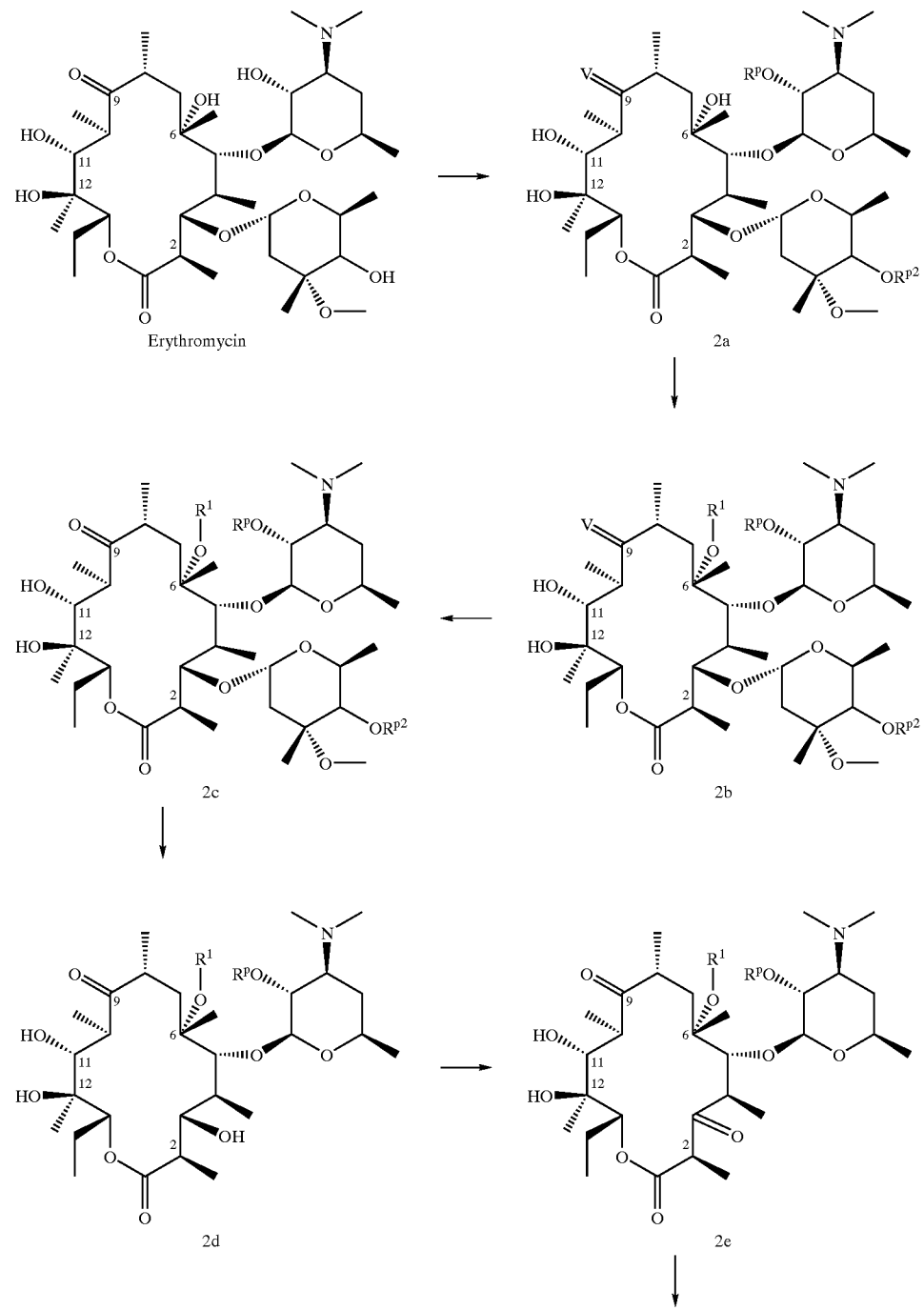

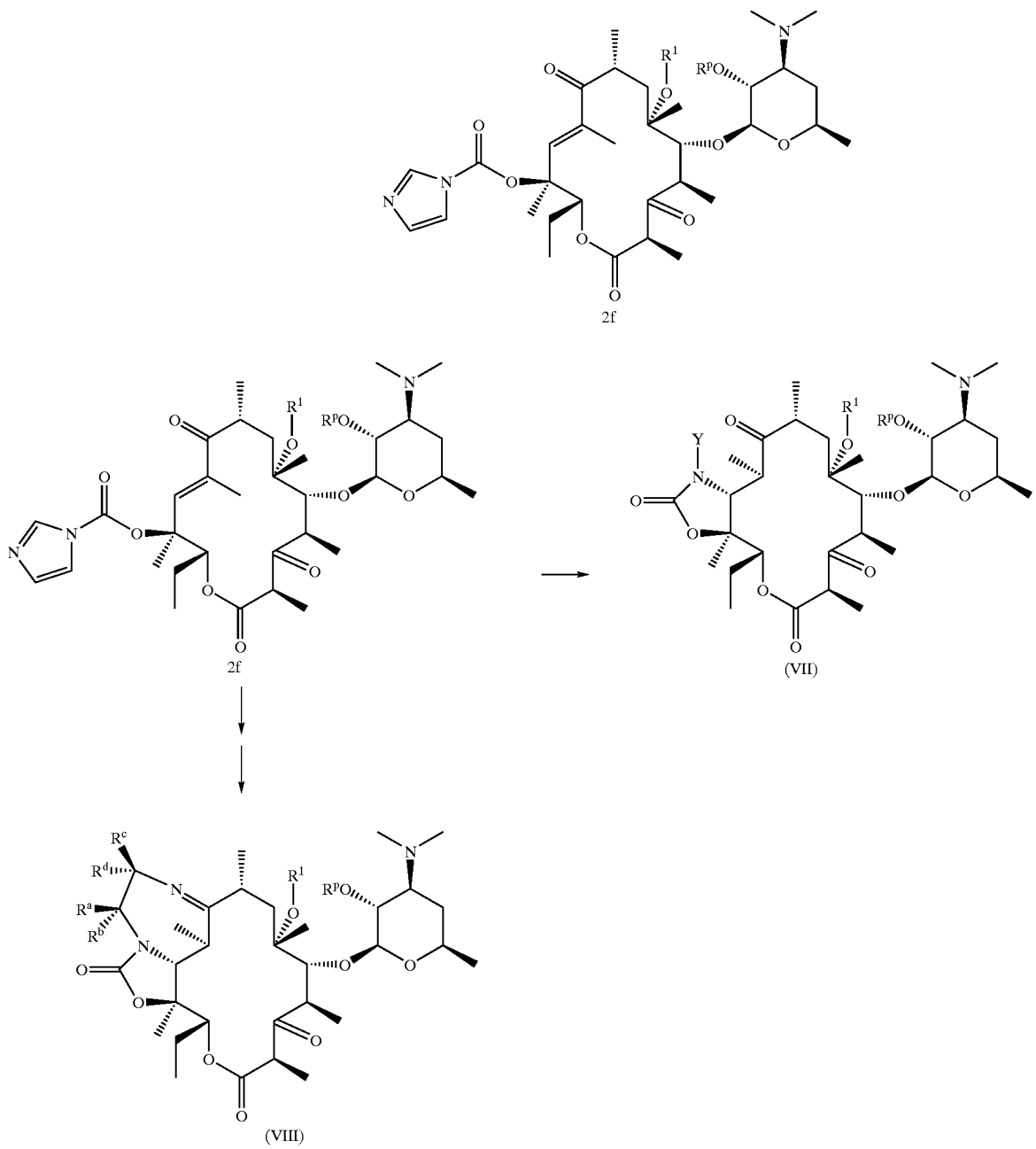

(VIII)

As illustrated in Scheme 2, the 2'-hydroxy, optionally the 4"-hydroxy, and the C9-oxime of the erythromycin derivative are protected to obtain 2a, wherein V, $R^p$ and $R^{p2}$ are as previously defined for the 2-norerythromycin substrate. Alkylation of 2a affords the 6-O-alkylated erythromycin derivative 2b, wherein $R^1$ is as previously defined. The intermediate 2b can be deoximated and optionally deprotected to give 2c. Removal of the cladinose sugar of 2c affords compound 2d. Oxidation of the resulting 3-hydroxy moiety of 2d yields a 6—O-alkyl ketolide derivative 2e. The compound 2e can be treated to obtain the 10,11-anhydro-12-imidazolyl compound 2f. The intermediate 2f can be converted to the 11,12-carbamate (VII) or the tricyclic imine (VIII), wherein Y, $R^a$, $R^b$, $R^c$ and $R^d$ are as previously defined. Compounds (VII) and (VIII) can be further derivatized by the methods described below to obtain compounds of formula (I) or (II).

Preparation of the 2—Nor-2-Substituted Ketolide Derivatives

Removal of the C2-methyl can be accomplished on the 6—O-alkyl ketolide derivatives (VII) or (VIII). An example of a procedure suitable for removing the methyl group from the 2-position is described below in Scheme 3.

Scheme 3

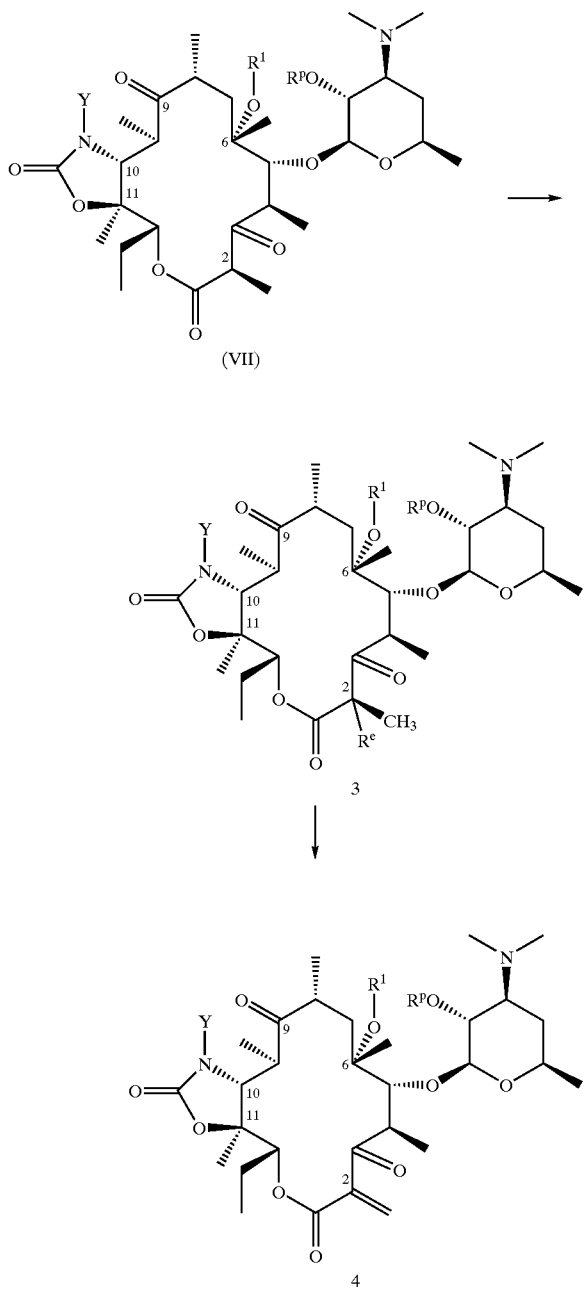

In accordance with Scheme 3, ketolide (VII) is treated with an electrophilic reagent to obtain intermediate 3, wherein $R^e$ is hydroxy, halide, sulfone, sulfoxide, sulfide, or selenide. In a preferred compound 3, $R^e$ is halide, phenyl sulfonyl, phenyl sulfoxide, phenyl sulfide or phenyl selenide.

Suitable reagents for providing a halide leaving group include, but are not limited to, N-bromosuccinimide, N-chlorosuccinimide, N-iodosuccinimide, bromine, chlorine, iodine, and the like. Reagents that allow for the introduction of sulfur leaving groups, wherein $R^e$ is sulfone, sulfoxide, or sulfide, are arylsulfonyl halides, arylsulfinic anhydride and aryl disulfides. Exemplary electrophilic sulfur reagents include, but are not limited to, phenylsulfonyl chloride, diphenyl disulfide, and the like. Likewise, for the introduction of selenium electrophiles, areneselenyl halides and diselenyl compounds, for example phenylselenyl chloride, diphenyl diselenide, can be used for the preparation of 3. The preferred reagent is phenylselenyl chloride.

Elimination of the C2-electrophile of 3 to give 4 can be accomplished in the following steps depending on the type of $R^e$. When $R^e$ is a halide, arylsulfoxide or arylsuphonyl, the elimination can be affected with the treatment of an amine base, for example 1,8-diazabicyclo[5.4.0]undec-7-ene (DBU) or Hunig's base, or with an hydroxy or alkoxy base. Suitable bases for the reaction are potassium hydroxide, tetraalkyl ammonium hydroxide, sodium tert-butoxide, potassium tert-butoxide, potassium trimethylsilyoxide, and the like.

The elimination of the intermediate wherein $R^1$ is an aryl sulfoxide can be carried out via a thermal elimination upon heating the reaction mixture to 70–150° C. When Re is an aryl sulfide, the sulfide is oxidized to a sulfoxide and the sulfoxide leaving group is eliminated by the method described above. The selenide, for example wherein Re is an aryl selenide, can be oxidized to a selenoxide, which spontaneously eliminates at room temperature to give compound 4.

The oxidation of the selenide or sulfide can be carried out using a monopersulfate reagent or a perbenzoic acid in an organic solvent. Exemplary organic solvents are dimethylformamide, dimethyl sulfoxide, dimethoxyethane, acetonitrile, tetrahydrofuran, dichloromethane, chloroform, methanol, ethanol, and the like, or mixtures thereof. Portions of water can be added to obtain an aqueous solution when a monopersulfate reagent is employed. Preferably, the solution is from about 40% to about 60% aqueous. The reaction can be accomplished with from about 1 to about 4 molar equivalents of the monopersulfate compound for each equivalent of ketolide 3. A preferred monopersulfate compound is commercially available as OXONE® (potassium peroxymonosulfate, DuPont). The preferred reaction is accomplished with about three equivalents of potassium peroxymonosulfate in a 50% aqueous solution of tetrahydrofuran.

Derivatization of the C2-substituent

The C2-methylene group can be derivatized to provide compounds of formula (I) or (II) by a variety of methods. Examples of suitable procedures for accomplishing the derivatization are shown below in Scheme 4.

Scheme 4

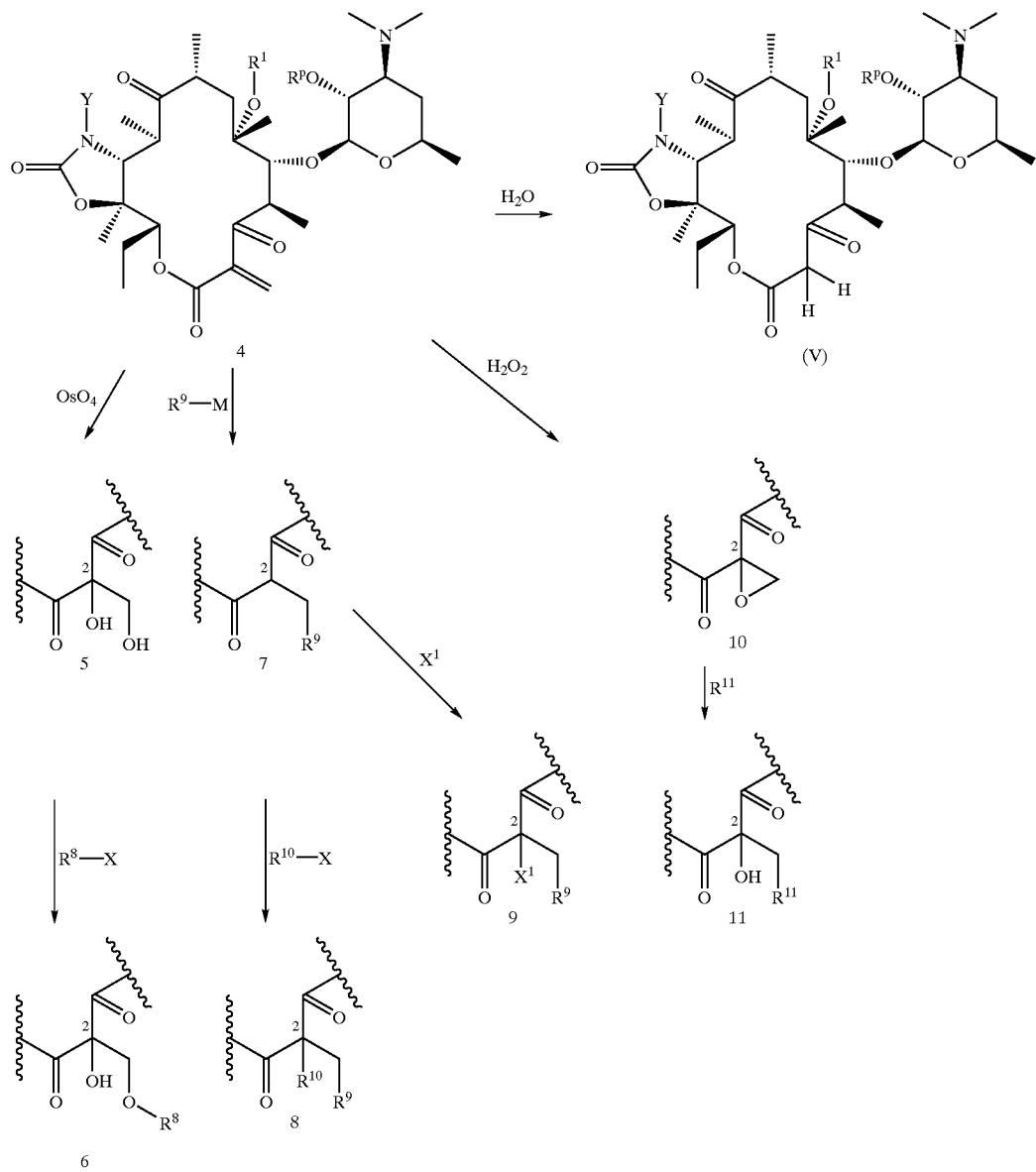

As illustrated in Scheme 4, the C2-methylene of compound 4 can be oxidized to the diol 5. The diol 5 can be selectively alkylated or acylated with a suitable reagent of the formula $R^8$-X, wherein $R^8$ is an alkyl, aryl, acyl or arylacyl group and X is a leaving group, for example, halogen, sulfonate, methanesulfonate, toluenesulfonate, or trifluoromethanesulfonate, in the presence of a base to obtain 6. A suitable base for the reaction is sodium hydride or sodium bis(trimethylsilyl) amide.

To directly modify the C2-position, a compound of formula 4 can be reacted with an organolithium or a Grignard reagent of the formula $R^9$-M, wherein $R^9$ is alkyl and M is a metal, in the presence of copper(I) reagent, for example copper(I) bromide, copper(I) iodide, copper(I) cyanide, and the like, to give the 1,4-addition product 7. Other nucleophiles are also suitable for the reaction. Examples of such nucleophiles include, but are not limited to, sodium enolate, allyl silane, allyl zinc, sodium malonate, sodium sulphonate, thiophenol, acetonitrile anion, sodium imidazole, and the like. Subsequent alkylation of compound 7 with a nitrogen electrophiles of the formula $R^{10}$-X, wherein $R^{10}$ is an electrophilic nitrogen group and X is a leaving group to give compound 8. Examples of electrophilic nitrogen reagents include but not limited to chloro amide ($ClNH_2$), diphenylphosphoryl amide ($Ph_2P(O)ONH_2$), toluenesulfonylazide ($TsN_3$), 2,4-dinitrophenylamine oxide((2,4-DNP)$ONH_2$). In addition compound 7 can be treated with a base such as sodium hydride or potassium tert-butoxide followed by reacting with an electrophilic halide, represented by $X^1$, to give compound 9.

Treatment of the C2-methylene of 4 with hydrogen peroxide affords an epoxide moiety of 10. Nucleophilic addition with a group $R^{11}$ to the epoxide of 10 can afford a C2-alcohol 11.

The intermediate 4 can be hydrolyzed to the intermediate of formula (V) to provide an additional intermediate for further C2-derivatization. The intermediate of formula (V) can also be obtained from 2-norerythromycin in the manner described for Scheme 1. Further modifications of the C2-position are shown below in Scheme 5.

Scheme 5

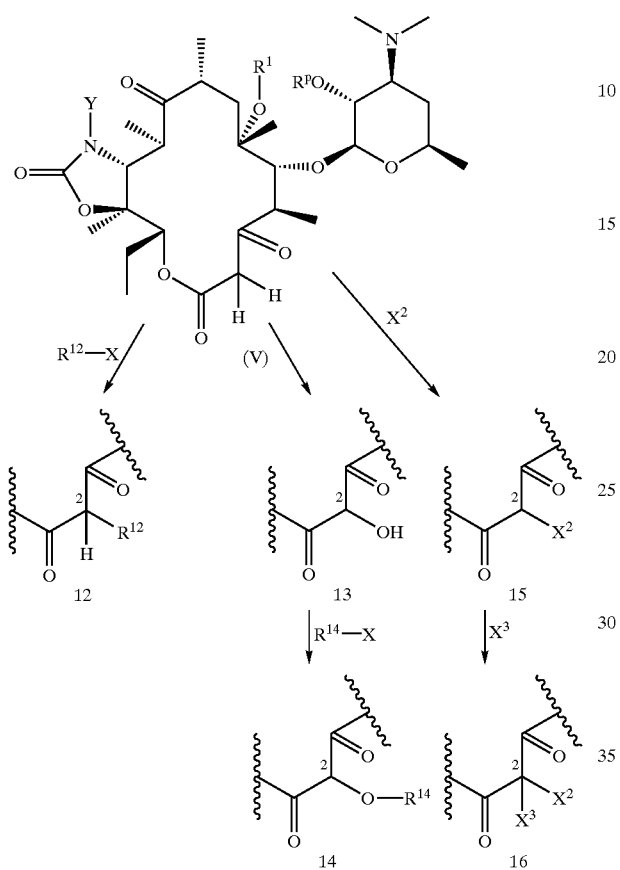

As shown in Scheme 5, alkylation of the compound of formula (V) affords the compound 12 under alkylation conditions previously described for modifying the C2-methylene moiety. The C2-position of (V) can be treated with osmium tetroxide to obtain the C2-hydroxy of 13. The intermediate 13 can be further alkylated or acylated with a reagent of formula $Rl^4$-X to obtain the compound 14.

In addition, the compound of formula (V) can be treated with a halogenating reagent in the present of a base to prepare compound 15. A suitable halogenating reagent is capable of replacing a hydrogen atom at the C2-position with a halogen atom. Various halogenating reagents can be used for the reaction. The preferred halogenating reagents are fluorinating reagents, for example N-fluorobenzenesulfonimide or $(CF_3SO_2)_2NF$. Methods for replacing the C2-hydrogen with a halogen atom are also discussed in PCT Publication No. WO 99/21871, which is herein incorporated by reference.

Treating compound 15 with a halogenating reagent under the conditions described above affords a compound of formula 16.

Compounds 4, 5, 6, 7, 8, 9, 10, 11, 12, 13, 14, 15, 16 and (V) are representative of C2-modified derivatives within the scope of formula (I). It will be readily apparent to one of skill in the art that the synthetic routes described above can be carried out with substitution of the substrate, reactants, or reagents to obtain compounds of formula (II). One of ordinary skill in the art will also recognize that other compounds within formula (I) and (II) can be synthesized by the substitution of the appropriate reactants and reagents in the syntheses shown in Schemes 3, 4 and 5.

Coupling of an Aromatic Group

6-O-alkenyl- and 6-O-alkynyl-substituted ketolide derivatives of erythromycin can be optionally coupled with an aromatic group to obtain compounds of formula (I) or (II), wherein $R^1$ is $C_1$–$C_6$ alkyl, $C_1$–$C_6$ alkenyl, or $C_1$–$C_6$ alkynyl optionally substituted with a group $R^2$, wherein $R^2$ is aryl, substituted aryl, heteroaryl, substituted heteroaryl, heterocycloalkyl, substituted heterocycloalkyl, or $Ar_1$–$Ar_2$, wherein $Ar_1$ and $Ar_2$ are as previously defined.

A compound having 6—O-substitution

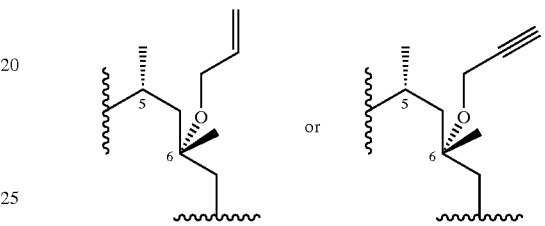

for example, can be coupled with a suitable aromatic group by methods of transition metal-catalyzed coupling. Methods for coupling aryl groups to the 6-O-alkenyl and 6-O-alkynyl groups, particularly 6—O-allyl and 6—O-propargyl, respectively, of macrolide derivatives are described in U.S. Pat. No. 5,866,549 and U.S. patent application Ser. No. 09/270,497, which are herein incorporated by reference.

A suitable aromatic group can be provided by an aromatic halide or aromatic trifluoromethanesulfonate reagent. Examples of such reagents include, but are not limited to, an aryl halide, substituted aryl halide, heteroaryl halide, or substituted heteroaryl halide, or a bifunctionalized aryl or heteroaryl precursor group.

Reaction of the allyl-substituted derivatives with an aryl halide is performed in the presence of Pd(II) or Pd(0) catalysts with promoters such as phosphines, arsines, amines, and inorganic bases in polar, aprotic solvents; see *Organic Reactions*, 1982, 27, 345–390. Preferably, the promoters are selected from the group consisting of triphenylphosphine, triphenylarsine, pyridine and triethylamine, potassium carbonate, and cesium fluoride. The aprotic solvents are as previously defined such as dimethylformamide, dimethyl sulfoxide, dimethylethane, acetonitrile, tetrahydrofuran, or mixtures thereof. The reaction is accomplished at temperatures from about room temperature to about 150° C., depending on the reagents chosen and the nature of the aryl halide.

The 6—O-propargyl groups can be derivatized under Sonagashira conditions by combining the alkyne derivative with an aryl halide in the presence of a phosphine promoter and Cu(I) optionally in the presence of an organic base. Preferably, the organic base is triethylamine. Summary of the procedures, reagents, and solvents for coupling terminal alkynes with aryl halides is described in *Tetrahedron Lett.*, 1975, 50, 4467–4470.

The propargyl carbamate derivatives can be derivatized with borane-THF in aprotic solvents at temperatures from about −20° C. to about room temperature to provide vinyl boronic acid derivatives. The vinyl boronic acid derivatives can be reacted under Suzuki conditions with aryl halide reagents, catalysts and promoters to provide allyl products similar to the Heck coupling reaction of the aryl halide as described above. A thorough discussion of Suzuki conditions is provided in *Chemical Reviews,* 1995, Vol. 95, No. 7, 2457–2483.

The Heck and Sonagashira conditions described above can also be used to couple aryl groups to allyl and propargyl groups at the C2-position of the macrolide. For example, a C2-allyl group can be reacted with an aryl halide in the presence of Pd(II) or Pd(0) catalysts with a promoter to afford a compound wherein $R^3$ is —$CH_2C$=$CH$—$R^2$, wherein $R^2$ is aryl, substituted aryl, heteroaryl, substituted heteroaryl, or $Ar_1$–$Ar_2$. Likewise, a C2-propargyl group can be treated under Sonagashira conditions with an aryl halide in the presence of a phosphine promoter and Cu(I) optionally in the presence of an organic base to give compounds wherein $R^3$ is a group —$CH_2C$≡$C$—$R^2$, and $R^2$ is aryl, substituted aryl, heteroaryl, substituted heteroaryl, or $Ar_1$–$Ar_2$.

It will be readily apparent to one of ordinary skill other compounds of formulae (I) and (II) can be synthesized by substitution of the appropriate reactants and agents in the syntheses described. It will also be apparent to one skilled in the art that the selective protection and deprotection steps, as well as the order of the steps themselves, can be carried out in varying order, depending on the nature of the substrate compound and the substituents.

Determination of Biological Activity

In Vitro Assay of Antibacterial Activity

Representative compounds of the present invention were assayed in vitro for antibacterial activity as follows: twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20–24 hours. In addition, a control plate using BHI agar with no test compound was prepared and incubated at the beginning and end of each test.

A plate containing erythromycin A was also prepared to provide test-to-test comparability. Erythromycin A has susceptibility patterns for the organisms being tested and belongs to the same antibiotic class as the test compounds.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1, demonstrate the antibacterial activity of the compounds of the invention.

| Microorganism | Code |
|---|---|
| Staphylococcus aureus ATCC 6538P | AA |
| Staphylococcus aureus A-5177 | BB |
| Staphylococcus aureus A-5278 | CC |
| Staphylococcus aureus CMX 642A | DD |
| Staphylococcus aureus NCTC 10649M | EE |
| Staphylococcus aureus CMX 553 | FF |
| Staphylococcus aureus 1775 | GG |
| Staphylococcus epidermidis 3519 | HH |
| Enterococcusfaecium ATCC X043 | II |
| Streptococcus bovis A-5169 | JJ |
| Streptococcus agalactiae CMX 508 | KK |

-continued

| Microorganism | Code |
|---|---|
| Streptococcus pyogenes EES61 | LL |
| Streptococcus pyogenes 930 | MM |
| Streptococcus pyogenes PIU 2548 | NN |
| Micrococcusluteus ATCC 9341 | OO |
| Micrococcusluteus ATCC 4698 | PP |
| Escherichiacoli JUHL | QQ |
| Escherichiacoli SS | RR |
| Escherichiacoli DC-2 | SS |
| Candida albicans CCH 442 | TT |
| Mycobacterium smegmatis ATCC 114 | UU |
| Nocardia Asteroides ATCC 99700 | VV |
| HaemophilisInfluenzae DILL AMP R | WW |
| Streptococcus Pneumonia ATCC 6303 | XX |
| Streptococcus Pneumonia GYR 1171 | YY |
| Streptococcus Pneumonia 5979 | ZZ |
| Streptococcus Pneumonia 5649 | ZA |

TABLE 1

Antibacterial Activity (MIC's) of Selected Compounds

| | Ery. A standard | Example 2 | Example 3 | Example 5 | Example 6 | Example 7 |
|---|---|---|---|---|---|---|
| AA | 0.2 | 0.39 | 0.05 | >100 | 0.39 | — |
| BB | 3.1 | 0.39 | 0.05 | >100 | 0.78 | — |
| CC | >100 | >100 | >100 | >100 | >100 | — |
| EE | 0.39 | 0.39 | 0.1 | >100 | 0.78 | — |
| GG | >100 | >100 | >100 | >100 | >100 | — |
| HH | 0.39 | 0.39 | 0.05 | >100 | 0.78 | — |
| JJ | 0.02 | 0.02 | 0.01 | 25 | 0.05 | — |
| KK | 0.05 | 0.02 | 0.01 | 100 | 0.2 | — |
| LL | 0.05 | 0.01 | 0.01 | 100 | 0.2 | — |
| MM | >100 | 50 | 12.5 | >100 | 25 | — |
| NN | 6.2 | 0.2 | 0.1 | >100 | 0.78 | — |
| PP | 0.2 | 0.2 | 0.05 | >100 | 0.39 | — |
| QQ | >100 | 100 | 50 | >100 | >100 | — |
| RR | 0.78 | 0.39 | 0.2 | >100 | 3.1 | — |
| TT | >100 | >100 | >100 | >100 | >100 | — |
| UU | 3.1 | 6.2 | 3.1 | >100 | 12.5 | — |
| VV | 0.1 | 0.2 | 0.05 | >100 | 0.2 | — |
| WW | 4 | 8 | 2 | >128 | 16 | 8 |
| XX | 0.06 | 0.03 | 0.008 | 32 | 0.25 | 0.03 |
| YY | 0.06 | 0.03 | ≦0.004 | 32 | 0.125 | 0.03 |
| ZZ | >128 | 8 | 64 | >128 | 64 | 64 |
| ZA | 16 | 0.5 | 0.25 | >128 | 2 | 0.25 |

The compounds and processes of the invention will be better understood in connection with the Examples, which are intended as an illustration of and not a limitation upon the scope of the invention as defined in the appended claims.

EXAMPLES

The Examples described herein may reference general experimental procedures for the coupling of aryl, substituted aryl, heteroaryl, substituted heteroaryl, and groups of the formula $Ar_1$–$Ar_2$ with the hydrocarbon group of $R^1$. The referenced methods, General Experimental Procedure A or B, are described below.

General Experimental Procedure A

General Experimental Procedure A can be used to accomplish the Heck reaction for preparing compounds of formula (XI) or (XIII), wherein Y is hydrogen; $R^p$ is hydrogen; $R^2$ is a substituent other than hydrogen that has been previously defined, for example, aryl, substituted aryl, heteroaryl, substituted heteroaryl, and $Ar_1$–$Ar_2$, wherein $Ar_1$ and $Ar_2$ are as previously defined; $R^3$ is hydrogen; and $R^4$ is hydrogen.

Step a: Compounds of Formula (XI) or (XIII), Y is Hydrogen, $R^p$ is Benzoyl, $R^2$ is Aryl $R^3$ is Hydrogen and $R^4$ is Hydrogen A mixture comprising a compound of formula (XI) or (XIII) wherein Y is hydrogen, $R^P$ is —C(O)CH$_3$ or —C(O)C$_6$H$_5$, and R$^2$, R$^3$ and R$^4$ are hydrogen (1 equivalent), Pd(OC(O)CH$_3$)$_2$ (0.2 equivalents), and tri-o-tolylphosphine (0.4 equivalents) in acetonitrile is degassed, flushed with nitrogen, treated sequentially with triethylamine (2 equivalents) and aryl halide (2 equivalents), heated at 80–90° C. for 24–48 hours (hrs.), diluted with ethyl acetate, washed sequentially with saturated aqueous NaHCO$_3$, brine, dried over Na$_2$SO$_4$, filtered, and concentrated. The residue is chromatographed on silica gel column to provide the 2'-protected title compound.

Step b: Compounds of Formula (XI) or (XIII), Y is Hydrogen, $R^P$ is Hydrogen, R$^2$ is aryl, R$^3$ is Hydrogen and R$^4$ is Hydrogen Compound of step a in 5 ml of methanol is stirred at room temperature (r.t.) for 1–5 days or is heated at reflux for 24 hrs. Removal of the solvent in vacuo and purification on silica gel column with a 5% solution of MeOH/CH$_2$Cl$_2$ (5% MeOH/CH$_2$Cl$_2$) to give the title compound.

General Experimental Procedure B

General Experimental Procedure B can be used to accomplish the Sonogashira reaction for preparing compounds of formula (XII) or (XIV), wherein Y is hydrogen; $R^P$ is hydrogen; R$^2$ is a substituent other than hydrogen that has been previously defined, for example, aryl, substituted aryl, heteroaryl, substituted heteroaryl, and Ar$_1$–Ar$_2$, wherein Ar$_1$ and Ar$_2$ are as previously defined; R$^3$ is hydrogen; and R$^4$ is hydrogen.

Step a: Compounds of Formula (XII) or (XIV), Y is Hydrogen, $R^P$ is Benzoyl, R$^2$ is not Hydrogen R$^3$ is Hydrogen and R$^4$ is Hydrogen A mixture of a compound of formula (XII) or (XIV), wherein Y is hydrogen, $R^P$ is —C(O)CH$_3$ or benzoyl, R$^2$, R$^3$ and R$^4$ are H (1 equivalent) and Pd(PPh$_3$)$_2$Cl$_2$ (0.02 equivalents) in 5:1 acetonitrile/triethylamine (5 ml:1 ml) is degassed and flushed with nitrogen, treated sequentially with CuI (0.01 equivalents) and an aryl halide or arylacyl halide (2–3 equivalents), stirred at room temperature for 10 minutes, heated at 70–90° C. for 6–48 hours, diluted with ethyl acetate or isopropyl acetate, washed sequentially with water and brine, dried over Na$_2$SO$_4$, and chromatographed on silica gel to give the title compound.

Step b: Compounds of Formula (XII) or (XIV), Y is Hydrogen, $R^P$ is Hydrogen, R$^2$ is not Hydrogen, R$^3$ is Hydrogen and R$^4$ is Hydrogen Compound of step a in 5 ml of methanol is stirred at r.t. for 1–5 days or is heated at reflux for 24 hrs. Removal of the solvent in vacuo and purification on silica gel column with 5% MeOH/CH$_2$Cl$_2$ give the title compound.

EXPERIMENTAL EXAMPLES

Examples 1–53 illustrate procedures suitable for preparing a compound within the scope of the invention.

Example 1

Compound of Formula (XI), $R^P$ is Benzoyl, Y is Hydrogen, R$^2$ is 3-quinolyl, R$^3$ and R$^4$ Taken Together is =CH$_2$ Step 1a: Compound of Formula (XI), $R^P$ is Benzoyl, Y is Hydrogen, R$^2$ is 3-quinolyl, R$^3$ is CH$_3$ and R$^4$ is PhSe (Scheme 3, Compound 3)

A solution of compound (XI), R$^1$ is benzoyl, Y is Hydrogen, R$^2$ is 3-quinolyl, R$^3$ is CH$_3$, and R$^4$ is hydrogen, prepared according to U.S. Pat. No. 5,866,549 (15 g, 17.2 mmol), in DMF (60 mL) at 0° C. was treated with small portions of NaH (60% in oil, unwashed, 1.37 g, 34.4 mmol). The reaction mixture was stirred at 0° C. for 45 minutes, treated over a period of ten minutes with PhSeCl (4.94 g, 25.8 mmol) in DMF (15 mL), stirred at 0° C. for 3 hours, treated with ethyl acetate (1 L), and washed sequentially with saturated NaHCO$_3$, water, and brine, dried (Na$_2$SO$_4$), filtered, and concentrated. The concentrate was purified by flash chromatography on silica gel with 2:1 hexanes/acetone to provide 14.4 g of the desired product.

$^{13}$C NMR (125 MHz, CDCl$_3$) δ 217.7, 205.9, 170.3, 165.4, 157.8, 149.3, 147.6, 137.9, 132.8, 132.5, 130.7, 130.2, 129.7, 129.6, 129.5, 129.2, 129.1, 129.0, 128.3, 128.0, 127.9, 126.8, 126.5, 99.4, 83.3, 79.7, 79.4, 77.8, 72.1, 68.7, 64.1, 63.3, 58.1, 57.9, 45.1, 44.1, 40.7, 39.0, 37.0, 31.7, 23.1, 22.5, 21.4, 20.9, 20.1, 18.2, 13.6, 13.5, 10.7.

High Resolution FAB MS calculated m/z for (M+H)$^+$ of C$_{55}$H$_{68}$N$_3$O$_{11}$Se: 1026.4019. Found: 1026.4009.

Step 1b: Compound of Formula (XI), $R^P$ is Hydrogen, Y is Hydrogen, R$^2$ is 3-quinolyl, R$^3$ and R$^4$ Taken Together is =CH$_2$ (Scheme 3, Compound 4)

To compound of step 1a (1.00 g, 0.976 mmol) in THF (10 ml) and water (10 ml) was added oxone (1.800 g, 2.93 mmol) and stirred at room temperature for 6 hrs. TLC still showed the presence of starting material. Additional oxone (600 mg) was added and stirred at room temperature for an additional 20 hrs. Then 10% aqueous NaHSO$_3$ was added and stirred at room temperature for 30 minutes, then treated with methane. The mixture was taken up in isopropyl acetate and washed with saturated aqueous Na$_2$CO$_3$. The organic extracts were washed with brine and dried over Na$_2$SO$_4$. Removal of the solvents in vacuo and purification on silica gel column with 2:1 hexanes/acetone gave the title compound and two additional products (Compound of formula (XI), $R^P$ is hydrogen, Y is Hydrogen, R$^2$ is 3-quinolyl, R$^3$ and R$^4$ taken together is —CH$_2$O—, and Compound of formula (XI), $R^P$ is hydrogen, Y is hydrogen, R$^2$ is 3-quinolyl, R$^3$ and R$^4$ is hydrogen)

MS (APCI+) m/z 868 (M+H)$^+$;

$^{13}$C NMR(125 MHz, CDC13) δ 217.3, 202.9, 165.4, 163.8, 157.6, 149.3, 147.6, 142.4, 135.0, 132.9, 132.6, 130.3, 129.7, 129.5, 129.2, 129.1, 128.4, 128.0, 126.9, 126.8, 100.8, 85.3, 79.6, 77.7, 75.6, 71.8, 69.4, 64.4, 61.3, 57.3, 46.4, 44.9, 40.7, 39.6, 36.9, 31.9, 29.2, 22.4, 20.1, 20.3, 18.3, 13.9, 13.7, 10.7.

Example 2

Compound of Formula (XI), $R^P$ is Hydrogen, Y is Hydrogen, R$^2$ is 3-quinolyl, R$^3$ is Hydrogen and R$^4$ is Hydrogen Step 2a: Compound of Formula (XI), $R^P$ is Benzoyl, Y is Hydrogen, R$^2$ is 3-quinolyl, R$^3$ is Hydrogen and R$^4$ is Hydrogen (Scheme 4, Compound (V))

The title compound was obtained as one of the product according to example 1, step 1 a and 1b, due to hydrolysis of the product of example 1, step 1b.

MS (APCI+) m/z 856 (M+H)$^+$;

$^{13}$C NMR(125 MHz, CDC13) δ 217.5, 202.1, 165.2, 164.8, 157.5, 149.7, 147.6, 132.9, 132.5, .130.4, 130.1, 129.7, 129.5, 129.2, 129.1, 128.4, 128.3, 128.0, 126.7, 101.0, 83.4, 78.9, 77.9, 76.5, 71.9, 69.2, 64.4, 63.5, 58.0, 48.5, 46.3, 44.8, 40.7, 38.9, 37.3, 31.4, 22.5, 21.0, 20.2, 18.0, 14.1, 13.6, 10.8.

Step 2b: Compound of Formula (XI), $R^P$ is Hydrogen, Y is Hydrogen, R$^2$ is 3-quinolyl, R$^3$ is Hydrogen and R$^4$ is Hydrogen Compound from step 2a (50 mg) was treated with methanol (2 ml) at r.t. for 5 days. Removal of the solvent in vacuo and purification on silica gel column with 5% MeOH/CH$_2$Cl$_2$ gave the title compound (32 mg).

$^{13}$C NMR(125 MHz, CDCl3) δ 217.5, 201.8, 164.9, 157.5, 149.7, 147.5, 132.6, 130.1, 129.5, 129.1, 128.5, 128.0, 126.7, 103.3, 83.5, 78.9, 77.9, 77.7, 70.2, 69.5, 65.8, 64.5, 58.0, 48.4, 47.1, 44.7, 40.2, 39.1, 37.4, 28.2, 22.5, 21.1, 20.3, 18.0, 14.2, 13.6, 10.8.

HRMS m/z calcd (M+H)$^+$ for C41H58N3O10: 752.4117. Found: 752.4115.

Example 3

Compound of Formula (I), R$^P$ is Hydrogen, Y is Hydrogen, R$^1$ is —CH$_2$CH(OH)CH(OH)—(3-quinolyl), R$^3$ is —CH$_2$OH and R$^4$ is OH Step 3a: Compound of formula (I), R$^P$ is Benzoyl, Y is Hydrogen, R$^1$ is —CH$_2$CH(OH)CH(OH)—(3-quinolyl), R$^3$ is —CH$_2$OH and R$^4$ is OH (Scheme 4, Compound 5)

To compound of example 1, step 1a (100 mg, 0.0976 mmol) and NMO (57.2 mg, 0.488 mmol) in THF (0.5 ml) and $^t$BuOH (0.5 ml) and water (10 μL) at r.t. was added OsO$_4$ (2.5% in $^t$BuOH, 122 μL, 0.00976 mmol). The reaction mixture was stirred at r.t. for 3 hrs., then 3 ml of 10% aqueous NaHSO$_3$ was added and stirred at r.t. for 4 hrs. The mixture was taken up in isopropyl acetate and washed with saturated aqueous NaHCO$_3$ (1×), water (2×), and brine (1×) and dried over Na$_2$SO$_4$. Removal of the solvents in vacuo gave the title compound.

MS (ESI+) m/z 936 (M+H)$^+$;

Step 3b: Compound of formula (I), R$^P$ is Hydrogen, Y is Hydrogen, R$^1$ is —CH$_2$CH(OH)CH(OH)—(3-quinolyl) R$^3$ is —CH$_2$OH and R$^4$ is OH Compound of step 3a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 4

Compound of formula (I), R$^P$ is hydrogen, Y is hydrogen, R$^1$ is —CH$_2$CH=O, R$^3$ is —CH$_2$OH and R$^4$ is OH Step 4a: Compound of formula (I), R$^P$ is Benzoyl, Y is Hydrogen, R$^1$ is —CH$_2$CH=O, R$^3$ is —CH$_2$OH and R$^4$ is OH To the crude compound of example 3, step 3a (70 mg, 0.0749 mmol) in THF (2.5 ml) and water (0.5 ml) at r.t. was added NaIO$_4$ (35 mg, 0.165 mmol). The reaction mixture was stirred at r.t. for 4 hrs. The mixture was taken up in isopropyl acetate and washed with saturated aqueous NaHCO$_3$ (1×), water (2×), and brine (1×) and dried over Na$_2$SO$_4$. Removal of the solvents in vacuo and purification on silica gel column with 3% MeOH/CH$_2$Cl$_2$ to 5% MeOH/CH$_2$Cl$_2$ gave the title compound (28 mg).

MS (ESI+) m/z 777 (M+H)$^+$;

Step 4b: Compound of Formula (I), R$^P$ is Benzoyl, Y is Hydrogen, R$^1$ is —CH=CH=O, R$^3$ is —CH$_2$OH and R$^4$ is OH Compound of step 4a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 5

Compound of Formula (XI), R$^P$ is Hydrogen, Y is Hydrogen, R$^2$ is 3-quinolyl R$^3$ is —CH$_2$CH=CH$_2$ and R$^4$ is hydrogen Step 5a: Compound of Formula (XI), R$^P$ is Benzoyl Y is Hydrogen R$^2$ is 3-quinolyl, R$^3$ is —CH$_2$CH=CH$_2$ and R$^4$ is hydrogen (Scheme 4, Compound 7)

To CuBr.DMS (8.3 mg) in THF (0.5 ml) at −78° C. was added vinyl magnesium bromide (1 M in THF, 0.40 ml) and the reaction mixture was stirred for 10 minutes. Then compound of example 1, step 1a, (25 mg) in THF (0.5 ml) was added and stirred at −78° C. for 3 hrs. then warmed to r.t. The mixture was taken up in isopropyl acetate and washed with water (1×), brine (1×) and dried over Na$_2$SO$_4$. Removal of the solvents in vacuo and purification on silica gel column with 2:1 hexanes/acetone to 1:1 hexanes/acetone gave the title compound (7 mg).

MS (APCI+) m/z 896 (M+H)$^+$;

$^{13}$C NMR(125 MHz, CDCl3) δ 217.4, 203.8, 167.9, 165.2, 157.6, 149.7, 147.6, 133.9, 132.8, 132.6, 130.5, 130.1, 129.7, 129.5, 129.1, 129.1, 128.3, 128.2, 128.0, 126.7, 118.2, 100.9, 83.4, 78.8, 78.1, 75.7, 72.0, 69.2, 64.4, 63.4, 58.1, 56.6, 46.2, 44.9, 40.7, 38.7, 37.2, 33.4, 31.5, 22.8, 21.0, 20.2, 18.0, 14.0, 13.6, 13.5, 11.0.

Step 5b: Compound of Formula (XI), R$^P$ is Hydrogen, Y is Hydrogen, R$^2$ is 3-quinolyl R$^3$ is —CH$_2$CH=CH$_2$ and R$^4$ is Hydrogen Compound of step 5a (6 mg) in 5 ml of methanol was stirred at r.t. for 5 days. Removal of the solvent in vacuo and purification on silica gel column with 5% MeOH/CH$_2$Cl$_2$ gave the title compound (3.4 mg).

MS (ESI+) m/z 792 (M+H)$^+$.

Example 6

Compound of Formula (XI), R$^P$ is Hydrogen, Y is Hydrogen, R$^2$ is 3-quinolyl, R$^3$ is —CH$_2$SO$_3$H and R$^4$ is Hydrogen Step 6a: Compound of Formula (XI), R$^P$ is Benzoyl, Y is Hydrogen, R$^2$ is 3-quinolyl, R$^3$ is —CH$_2$SO$_3$H and R$^4$ is Hydrogen To compound of example 1, step 1a, (10.0 g, 9.76 mmol) in THF (40 ml) and water (30 ml) at 0° C. was added oxone (18.0 g, 29.3 mmol) as a solid and stirred at r.t. for 6 hrs. Then the mixture was diluted with 50 ml of CH$_2$Cl$_2$, cooled to 0° C. and added 100 ml of 20% aqueous NaHSO$_3$ and stirred for 10 min at 0° C. and 1.5 hrs. at r.t. The mixture was cooled to 0° C. and basified to pH 10–11 with 2N NaOH. The mixture was extracted with CH$_2$Cl$_2$ (3×), and was washed with saturated aqueous NaHCO$_3$ (1×), brine (2×) and dried over Na$_2$SO$_4$. Removal of the solvent in vacuo and purification on silica gel column with 1:1 hexanes/acetone to 100% acetone to 10% MeOH/acetone gave the title compound (Q30%) as one of the major products.

MS (ESI+) m/z 950 (M+H)$^+$;

$^{13}$C NMR(125 MHz, CDCl3) δ 216.9, 208.3, 204.0, 167.3, 164.6, 156.9, 149.8, 146.9, 133.2, 132.5, 130.4, 129.8, 129.4, 129.3, 129.0, 128.7, 128.5, 128.2, 127.6, 127.5, 126.6, 100.2, 83.3, 78.5, 78.2, 74.8, 71.7, 68.5, 63.8, 62.4, 57.8, 55.8, 53.4, 50.7, 46.0, 44.5, 40.3, 37.8, 36.7, 32.0, 30.3, 29.6, 22.4, 20.8, 20.1, 17.5, 13.7, 13.2, 13.1, 11.3.

Step 6b: Compound of Formula (XI), R$^P$ is Hydrogen, Y is Hydrogen, R$^2$ is 3-quinolyl R$^3$ is —CH SO$_3$H and R$^4$ is Hydrogen Compound of step 6a (300 mg) in 10 ml of methanol was heat reflux for 6 hrs. Removal of the solvent in vacuo and purification on silica gel column with 10–20% MeOH/acetone gave the title compound (213 mg).

$^{13}$C NMR(125 MHz, CDCl3) δ 218.0, 203.5, 167.5, 157.9, 149.2, 146.8, 133.4, 130.7, 129.4, 129.3, 128.1, 128.0, 127.5, 127.0, 103.6, 83.9, 79.3, 78.6, 76.4, 70.2, 69.1, 65.1, 64.2, 58.4, 53.8, 53.1, 49.2, 46.5, 45.0, 39.9, 39.0, 37.2, 31.6, 29.0, 28.5, 22.9, 21.0, 19.9, 17.8, 13.7, 13.5, 13.4, 11.1.

HRMS m/z calcd (M+H)$^+$ for C42H60N3O13S: 846.3841. Found: 846.3827.

Example 7

Compound of Formula (XI), R$^p$ is Hydrogen Y is Hydrogen R$^2$ is 3-quinolyl, R$^3$ is —CH CH (CO$_2$Me)$_2$ and R$^4$ is Hydrogen Step 7a: Compound of Formula (XI), R$^p$ is Benzoyl, Y is Hydrogen, R$^2$ is 3-quinolyl R$^3$ is —CH$_2$CH(CO$_2$Me)$_2$ and R$^4$ is Hydrogen To compound of example 1, step 1a, (300 mg, as a crude mixture) and dimethyl malonate (0.2 ml) in THF (2 ml) at r.t. was treated with KO$^t$Bu (1M in THF, 0.5 ml) and stirred for 24 hrs. The mixture was taken up in isopropyl acetate and washed with water (1×), brine (1×) and dried over Na$_2$SO$_4$. Removal of the solvents in vacuo and purification on silica gel column with 1:1 hexanes/EtOAc gave the title compound.

MS (ESI+) m/z 1000 (M+H)$^+$;

Step 7b: Compound of Formula (XI), R$^p$ is Hydrogen, Y is Hydrogen, R$^2$ is 3-quinolyl R$^3$ is —CH$_2$CH(CO$_2$Me)$_2$ and R$^4$ is Hydrogen Compound of step 7a (90 mg) in 5 ml of methanol was stirred at r.t. for 5 days. Removal of the solvent in vacuo and purification on silica gel column with 5% MeOH/CH$_2$Cl$_2$ gave the title compound.

MS (ESI+) m/z 896 (M+H)$^+$;

$^3$C NMR(125 MHz, CDC13) δ 217.5, 203.7, 169.0, 168.9, 167.8, 157.6, 149.7, 147.6, 132.6, 130.3, 129.4, 129.1, 129.1, 128.1, 128.0, 103.1, 83.5, 78.7, 78.5, 76.2, 70.2, 69.6, 65.9, 64.5, 58.1, 54.0, 52.7, 48.7, 46.6 45.0, 40.2, 39.1, 37.3, 28.3, 28.1, 22.8, 21.2, 20.2, 18.1, 13.9, 13.7, 13.6, 11.0.

Example 8

Compound of formula (XI), R$^p$ is hydrogen Y is Hydrogen, R$^2$ is 3-quinolyl R$^3$ and R$^4$ Taken Together is —CH$_9$O—

Step 8a: Compound of Formula (XI), R$^p$ is Benzoyl, Y is Hydrogen, R$^2$ is 3-quinolyl R$^3$ and R$^4$ Taken Together is —CH$_2$O— (Scheme 4, Compound 10)

The title compound was obtained as one of the products according to example 1, step 1b, due to over oxidation by oxone.

Alternatively, compound of example 1, step 1a, (80 mg) in CH$_2$Cl$_2$ (1 ml) was treated with 30% H$_2$O$_2$ (0.2 ml) at r.t. for 2 hrs., then 10% aqueous NaHSO$_3$ was added and stirred at room temperature for 30 minutes. The mixture was taken up in isopropyl acetate and washed with saturated aqueous NaHCO$_3$ (2×), water (1×), brine (1×) and dried over Na$_2$SO$_4$. Removal of the solvents in vacuo and purification on silica gel column with 2:1 hexanes/acetone gave the title compound (22 mg) as a mixture of 2:1 diastereomers.

MS (APCI+) m/z 884 (M+H)$^+$;

$^{13}$C NMR(125 MHz, CDCl3) δ (218.0, 217.4), (203.0, 200.6), (166.0, 165.3), (165.1, 163.6), (157.4, 156.8), 149.4, (147.6, 147.5), 132.8, 132.6, 132.5, 130.3, 129.8, 129.7, 129.5, 129.4, 129.1, 128.3, 128.2, 128.1, 128.0, 127.9, 126.8, (101.9, 100.5), 83.5, 83.3, 81.9, 79.9, 79.4, 78.7, 77.3, (72.0, 71.7), 69.3, (65.1, 64.1), (63.4, 63.2), (59.1, 58.3), (58.5, 57.5), (52.0, 51.2), (45.1, 44.1), (40.2, 39.7), (40.0, 39.3), (37.8, 37.2), (28.2, 28.2), (22.1, 21.6), (21.0, 20.9), (20.4, 20.0), (18.2, 17.7), 16.7, 14.1, 13.6, 13.6, 13.4, 13.2, (10.6, 10.4).

Step 8b: Compound of Formula (XI), R$^p$ is hydrogen Y is hydrogen R$^2$ is 3-quinolyl R$^3$ and R$^4$ taken together is —CH$_2$O—

Compound from step 8a (20 mg) was treated with methanol (2 ml) at r.t. for 2 days. Removal of the solvent in vacuo and purification on silica gel column with 2–3% MeOH/CH$_2$Cl$_2$ gave the title compound as a mixture of 2:1 diastereomers (10 mg).

$^{13}$C NMR(125 MHz, CDCl3) δ (218.0, 217.7), (202.3, 200.8), (166.0, 163.6), (157.5, 156.8), 149.4, (147.6, 147.5), 132.6, 132.5, 129.8, 129.7, 129.6, 129.5, 129.1, 128.1, 128.0, 127.9, 126.8, (104.3, 103.1), 83.6, 83.5, 83.3, 80.2, 79.9, 79.6, 79.0, 78.5, 70.2, 70.1, 69.6, (65.7, 65.6), (65.1, 64.0), (59.4, 58.1), (58.6, 57.7), (52.2, 51.2), (46.1, 45.2), 44.0, 40.6, (39.9, 39.5), 39.5, (37.7, 37.0), (31.5, 31.3), (22.1, 21.6), (20.8, 20.7), (20.3, 20.0), (18.2, 17.7), 16.1, 14.0, 13.5, 13.6, 13.3, 12.6, (10.6, 10.3).

HRMS m/z calcd (M+H)$^+$ for C42H58N3O11: 780.4066. Found: 780.4065.

Example 9

Compound of Formula (XI), R$^p$ is Hydrogen, Y is Hydrogen, R$^2$ is 3-quinolyl, R$^3$ is F and R$^4$ is Hydrogen Step 9a: Compound of Formula (XI), R$^p$ is Benzoyl, Y is Hydrogen, R$^2$ is 3-quinolyl R$^3$ is F and R$^4$ is Hydrogen To compound of example 2, step 2a (1 mmol) in DMF (5 ml) at 0° C. is added NaH (2 mmol) and stirred for 30 minutes then (PhSO$_2$)$_2$NF (1.1 mmol) is added and stirred at 0° C. for 2–4 hrs. The mixture is taken up in isopropyl acetate and is washed with saturated aqueous NaHCO$_3$ (1×), water (2×), and brine (1×) and dried over Na$_2$SO$_4$. Removal of the solvents in vacuo and purification on silica gel column with 1:1 hexanes/acetone give the title compound.

Step 9b: Compound of Formula (XI), R$^p$ is Hydrogen, Y is Hydrogen R$^2$ is 3-quinolyl R$^3$ is F and R$^4$ is Hydrogen Compound of step 9a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 10

Compound of Formula (XI), R$^p$ is Hydrogen, Y is Hydrogen, R$^2$ is 3-quinolyl, R$^3$ is F and R$^4$ is F Step 10a: Compound of Formula (XI), R$^p$ is Benzoyl, Y is Hydrogen R$^2$ is 3-quinolyl, R$^3$ is F and R$^4$ is F To compound of example 2, step 2a (1 mmol) in CH$_2$Cl$_2$ (5 ml) at r.t. is added (CF$_3$SO$_2$)$_2$NF (2.1 mmol) (prepared according to the literature procedure: Z. Q. Xu et. al. J Chem. Soc. Chem. Comm. 1991, 179.) and is stirred at r.t. for 4–8 hrs. The mixture is taken up in isopropyl acetate and is washed with saturated aqueous NaHCO$_3$ (1×), water (2×), and brine (1×) and dried over Na$_2$SO$_4$. Removal of the solvents in vacuo and purification on silica gel column with 1:1 hexanes/acetone give the title compound.

Step 10b: Compound of Formula (XI), R$^p$ is Hydrogen, Y is Hydrogen R$^2$ is 3-quinolyl, R$^3$ is F and R$^4$ is F Compound of step 10a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 11

Compound of Formula (XI), R$^p$ is Hydrogen, Y is Hydrogen, R$^2$ is 3-quinolyl R$^3$ is —CH$_2$F and R$^4$ is F Step 11a: Compound of Formula (XI), R$^p$ is Benzoyl, Y is Hydrogen, R$^2$ is 3-quinolyl R$^3$ is —CH$_2$F and R$^4$ is F To compound of example 2, step 2a (1 mmol) in CH$_2$Cl$_2$ (5 ml) at 0° C. is added F$_2$ gas via bubbling in F$_2$ gas for 10 minutes then stirs at 0° C. for 2–4 hrs. and r.t. for 4 hrs. The mixture is taken up in isopropyl acetate and is washed with saturated aqueous $NaHCO_3$ (1×), water (2×), and brine (1×) and dried over $Na_2SO_4$. Removal of the solvents in vacuo and purification on silica gel column with 1:1 hexanes/acetone give the title compound.

Step 11b: Compound of Formula (XI), $R^p$ is Hydrogen, Y is Hydrogen, $R^2$ is 3-quinolyl, $R^3$ is —$CH_2F$ and $R^4$ is F Compound of step 11a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 12

Compound of Formula (XI), $R^p$ is Hydrogen, Y is Hydrogen, $R^2$ is Hydrogen, $R^3$ is hydrogen and $R^4$ is hydrogen Step 12a: Compound of Formula (XI), $R^p$ is benzoyl, Y is Hydrogen, $R^2$ is Hydrogen, $R^3$ is Hydrogen and $R^4$ is Hydrogen The title compound is prepared according to the procedure of examples 1 and 2 starting with compound of formula (XI), $R^p$ is benzoyl, Y is hydrogen, $R^2$ is hydrogen, $R^3$ is $CH_3$ and $R^4$ is hydrogen, which can be prepared according to U.S. Pat. No. 5,866,549.

Step 12b: Compound of Formula (XI), $R^p$ is Hydrogen, Y is Hydrogen, $R^2$ is Hydrogen, $R^3$ is Hydrogen and $R^4$ is Hydrogen Compound of step 12a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 13

Compound of Formula (XII), $R^p$ is hydrogen, Y is Hydrogen, $R^2$ is Hydrogen, $R^3$ is Hydrogen and $R^4$ is Hydrogen Step 13a: Compound of Formula (XII), $R^p$ is Benzoyl, Y is Hydrogen, $R^2$ is Hydrogen, $R^3$ is Hydrogen and $R^4$ is Hydrogen The title compound is prepared according to the procedure of examples 1 and 2 starting with compound of formula (XII), $R^p$ is benzoyl, Y is hydrogen, $R^2$ is hydrogen, $R^3$ is $CH_3$ and $R^4$ is hydrogen, which can be prepared according to U.S. Pat. No. 5,866,549.

Step 13b: Compound of Formula (XII), $R^p$ is Hydrogen, Y is Hydrogen, $R^2$ is Hydrogen, $R^3$ is Hydrogen and $R^4$ is Hydrogen Compound of step 13a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 14

Compound of Formula (XII), $R^p$ is Hydrogen, Y is Hydrogen, $R^2$ is Hydrogen, $R^3$ is Hydroxy and $R^4$ is Hydrogen Step 14a: Compound of Formula (XII), $R^p$ is Acetyl, Y is Hydrogen, $R^2$ is Hydrogen, $R^3$ is Hydroxy and $R^4$ is Hydrogen To compound of example 13, step 13a (0.1 mmol) and NMO (0.5 mmol) in THF (0.5 ml) and $^tBuOH$ (0.5 ml) and water (10 μL) at r.t. was added OS04 (2.5% in $^tBuOH$, 0.01 mmol). The reaction mixture was stirred at r.t. for 3 hrs., then 3 ml of 10% aqueous $NaHSO_3$ was added and stirred at r.t. for 4 hrs. The mixture was taken up in isopropyl acetate and washed with saturated aqueous $NaHCO_3$ (1×), water (2×), and brine (1×) and dried over $Na_2SO_4$. Removal of the solvents in vacuo gave the title compound.

Step 14b: Compound of Formula (XII), $R^p$ is Hydrogen, Y is Hydrogen, $R^2$ is Hydrogen, $R^3$ is Hydroxy and $R^4$ is Hydrogen Compound of step 14a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 15

Compound of Formula (XIII), $R^p$ is hydrogen, $R^2$ is Hydrogen, $R^3$ is Hydrogen, $R^4$ is Hydrogen, $R^a$ is Hydrogen, $R^b$ is Hydrogen, $R^c$ is Hydrogen and $R^d$ is Hydrogen Step 15a: Compound of Formula (XIII), $R^p$ is Benzoyl, $R^2$ is Hydrogen, $R^3$ is Hydrogen, $R^4$ is Hydrogen, $R^a$ is Hydrogen, $R^b$ is Hydrogen, $R^c$ is Hydrogen and $R^d$ is Hydrogen The title compound is prepared according to the procedure of examples 1 and 2 starting with compound of formula (XIII), $R^p$ is benzoyl, $R^2$ is hydrogen, $R^3$ is $CH_3$ and $R^4$ is hydrogen, and $R^a$, $R^b$, $R^c$, $R^d$ is hydrogen, which can be prepared according to PCT Publication Nos. WO 93/21200 and WO 98/30574.

Step 15b: Compound of Formula (XIII), $R^p$ is Hydrogen, $R^2$ is Hydrogen, $R^3$ is Hydrogen, $R^4$ is Hydrogen, $R^a$ is Hydrogen, $R^b$ is Hydrogen, $R^c$ is Hydrogen $R^d$ is Hydrogen Compound of step 15a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 16

Compound of Formula (XIV), $R^p$ is Hydrogen, $R^2$ is Hydrogen, $R^3$ is Hydrogen, $R^4$ is Hydrogen, $R^a$ is Hydrogen, $R^b$ is Hydrogen, $R^c$ is Hydrogen and $R^d$ is Hydrogen Step 16a: Compound of Formula (XIV), $R^p$ is Benzoyl, $R^2$ is Hydrogen $R^3$ is Hydrogen, $R^4$ is Hydrogen, $R^a$ is Hydrogen, $R^b$ is Hydrogen, $R^c$ is Hydrogen and $R^d$ is Hydrogen The title compound is prepared according to the procedure of examples 1 and 2 starting with compound of formula (XIV), $R^p$ is benzoyl, $R^2$ is hydrogen, $R^3$ is $CH_3$, $R^4$ is hydrogen, and $R^a$, $R^b$, $R^c$, $R^d$ is hydrogen, which can be prepared according to PCT Publication Nos. WO 93/21200 and WO 98/30574.

Step 16b: Compound of Formula (XIV), $R^p$ is Hydrogen, $R^2$ is Hydrogen, $R^3$ is Hydrogen, $R^4$ is Hydrogen, $R^a$ is Hydrogen, $R^b$ is Hydrogen, $R^c$ is Hydrogen and $R^d$ is Hydrogen Compound of step 16a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 17

Compound of Formula (XII), $R^p$ is Hydrogen, Y is Hydrogen, $R^2$ is 3-quinolyl $R^3$ is Hydrogen and $R^4$ is Hydrogen The title compound is prepared from the compound of example 13, step 13a, by following the General Experimental Procedure B for the Sonagashira reaction.

Example 18

Compound of Formula (XIII), $R^p$ is Hydrogen, $R^2$ is 3-quinolyl, $R^3$ is Hydrogen, $R^4$ is Hydrogen, $R^a$ is Hydrogen, $R^b$ is Hydrogen, $R^c$ is Hydrogen and $R^d$ is Hydrogen The title compound is prepared from the compound of example 15, step 15a, by following the General Experimental Procedure A for the Heck reaction.

Example 19

Compound of Formula (XIV), $R^p$ is Hydrogen, $R^2$ is 3-quinolyl, $R^3$ is Hydrogen, $R^4$ is Hydrogen, $R^a$ is Hydrogen, $R^b$ is Hydrogen, $R^c$ is Hydrogen and $R^d$ is Hydrogen The title compound is prepared from the compound of example 16, step 16a, by following the General Experimental Procedure B for the Sonagashira reaction.

Example 20

Compound of Formula (XI), $R^p$ is Hydrogen, Y is Hydrogen, $R^2$ is Hydrogen, $R^3$ is F and $R^4$ is Hydrogen Step 20a: Compound of Formula (XI), $R^p$ is Benzoyl, Y is Hydrogen, $R^2$ is Hydrogen, $R^3$ is F, $R^4$ is Hydrogen The title compound is prepared according to the procedures of examples 1, 2 and 9 starting from the compound of formula (XI), wherein $R^p$ is benzoyl, Y is hydrogen, $R^2$ is hydrogen, R is $CH_3$ and $R^4$ is hydrogen, which is prepared according to literature patent procedure U.S. Pat. No. 5,866,549.

Step 20b: Compound of Formula (XI), $R^p$ is Hydrogen, Y is Hydrogen, $R^2$ is Hydrogen, $R^3$ is F, $R^4$ is Hydrogen Compound of step 20a in 5 ml of methanol is stirred at r.t. for 5 days or is heated at reflux for 24 hrs. Removal of the solvent in vacuo and purification on silica gel column with 5% MeOH/$CH_2Cl_2$ give the title compound.

Example 21

Compound of Formula (XII), $R^p$ is Hydrogen, Y is Hydrogen, $R^2$ is Hydrogen, $R^3$ is F and $R^4$ is Hydrogen Step 21 a: Compound of Formula (XII), $R^p$ is Benzoyl, Y is Hydrogen, $R^2$ is Hydrogen, $R^3$ is F and $R^4$ is Hydrogen The title compound is prepared according to the procedures of example 1, 2 and 9 starting from the compound of formula (XII), wherein $R^p$ is benzoyl, Y is hydrogen, $R^2$ is hydrogen, $R^3$ is $CH_3$ and $R^4$ is hydrogen, which is prepared according to literature patent procedure U.S. Pat. No. 5,866,549.

Step 21b: Compound of Formula (XII), $R^p$ is Hydrogen, Y is Hydrogen, $R^2$ is Hydrogen $R^3$ is F and $R^4$ is Hydrogen Compound of step 21 a in 5 ml of methanol is stirred at r.t. for 5 days or is heated at reflux for 24 hrs. Removal of the solvent in vacuo and purification on silica gel column with 5% MeOH/$CH_2Cl_2$ give the title compound.

Example 22

Compound of Formula (XIII), $R^p$ is Hydrogen $R^2$ is hydrogen, $R^3$ is F, $R^4$ is Hydrogen $R^a$ is Hydrogen, $R^b$ is Hydrogen, $R^c$ is Hydrogen and $R^d$ is Hydrogen Step 22a: Compound of Formula (XIII), $R^p$ is Benzoyl, $R^2$ is Hydrogen, $R^3$ is F, $R^4$ is Hydrogen, $R^a$ is Hydrogen, $R^b$ is Hydrogen, $R^c$ is Hydrogen and $R^d$ is Hydrogen The title compound is prepared according to the procedures of example 1, 2 and 9 starting from the compound of formula (XIII), wherein $R^p$ is benzoyl, $R^2$ is hydrogen, $R^3$ is $CH_3$, $R^4$ is hydrogen and $R^a$, $R^b$, $R^c$ and $R^d$ are hydrogen, which can be prepared according to the procedures described in U.S. Pat. No. 5,866,549.

Step 22b: Compound of Formula (XIII) $R^p$ is Hydrogen, $R^2$ is Hydrogen, $R^3$ is F, $R^4$ is Hydrogen, $R^a$ is Hydrogen, $R^b$ is Hydrogen, $R^c$ is Hydrogen and $R^d$ is Hydrogen Compound of step 22a in 5 ml of methanol is stirred at r.t. for 5 days or is heated at reflux for 24 hrs. Removal of the solvent in vacuo and purification on silica gel column with 5% MeOH/$CH_2Cl_2$ give the title compound.

Example 23

Compound of Formula (XIV), $R^p$ is Hydrogen, $R^2$ is hydrogen, $R^3$ is F, $R^4$ is Hydrogen, $R^a$ is Hydrogen, $R^b$ is Hydrogen, $R^c$ is Hydrogen and $R^d$ is Hydrogen Step 23a: Compound of Formula (XIV), $R^p$ is Benzoyl, $R^2$ is Hydrogen, $R^3$ is F, $R^4$ is Hydrogen, $R^a$ is Hydrogen, $R^b$ is Hydrogen, $R^c$ is Hydrogen and $R^d$ is Hydrogen The title compound is prepared according to the procedures of example 1, 2 and 9 starting from the compound of formula (XIV), wherein $R^p$ is benzoyl, $R^2$ is hydrogen, $R^3$ is $CH_3$, $R^4$ is hydrogen and $R^a$, $R^b$, $R^c$ and $R^d$ are hydrogen, which can be prepared according to the procedures described in U.S. Pat. No. 5,866,549.

Step 23b: Compound of Formula (XIV), $R^p$ is Hydrogen, $R^2$ is Hydrogen, $R^3$ is F, $R^4$ is Hydrogen, $R^a$ is Hydrogen, $R^b$ is Hydrogen, $R^c$ is Hydrogen and $R^d$ is Hydrogen Compound of step 23a in 5 ml of methanol is stirred at r.t. for 5 days or is heated at reflux for 24 hrs. Removal of the solvent in vacuo and purification on silica gel column with 5% MeOH/$CH_2Cl_2$ give the title compound.

Example 24

Compound of Formula (XI), $R^p$ is Hydrogen, Y is Hydrogen, $R^2$ is Hydrogen, $R^3$ is F and $R^4$ is F Step 24a: Compound of Formula (XI), $R^p$ is Benzoyl, Y is Hydrogen, $R^2$ is Hydrogen, $R^3$ is F, $R^4$ is hydrogen The title compound is prepared according to the procedures of examples 1, 2 and 10 starting from the compound of formula (XI), wherein $R^p$ is benzoyl, Y is hydrogen, $R^2$ is hydrogen, $R^3$ is $CH_3$ and $R^4$ is hydrogen, which can be prepared according to the procedures described in U.S. Pat. No. 5,866,549.

Step 24b: Compound of Formula (XI), $R^p$ is Hydrogen, Y is Hydrogen, $R^2$ is Hydrogen, $R^3$ is F, $R^4$ is F Compound of step 24a in 5 ml of methanol is stirred at r.t. for 5 days or is heated at reflux for 24 hrs. Removal of the solvent in vacuo and purification on silica gel column with 5% MeOH/$CH_2Cl_2$ give the title compound.

Example 25

Compound of Formula (XII), $R^p$ is Hydrogen, Y is Hydrogen, $R^2$ is Hydrogen, $R^3$ is F and $R^4$ is F Step 25a: Compound of Formula (XII) $R^p$ is Benzoyl, Y is Hydrogen, $R^2$ is Hydrogen, $R^3$ is F and $R^4$ is F The title compound is prepared according to the procedures of examples 1, 2 and 10 starting from the compound of formula (XII), wherein $R^p$ is benzoyl, Y is hydrogen, $R^2$ is hydrogen, $R^3$ is $CH_3$ and $R^4$ is hydrogen which is prepared according to literature patent procedure U.S. Pat. No. 5,866,549.

Step 25b: Compound of Formula (XII), $R^p$ is Hydrogen, Y is Hydrogen, $R^2$ is Hydrogen, $R^3$ is F and $R^4$ is F Compound of step 25a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 26

Compound of Formula (XIII), $R^p$ is Hydrogen, $R^3$ is F, $R^4$ is F, $R^a$ is Hydrogen, $R^b$ is Hydrogen, $R^c$ is Hydrogen and $R^d$ is Hydrogen Step 26a: Compound of Formula (XIII), $R^p$ is benzoyl, $R^2$ is hydrogen, $R^3$ is F, $R^4$ is F, $R^a$ is hydrogen, $R^b$ is Hydrogen, $R^c$ is hydrogen and $R^d$ is hydrogen The title compound is prepared according to the procedures of examples 1, 2 and 10 starting from the compound of formula (XIII), wherein $R^p$ is benzoyl, $R^2$ is hydrogen, $R^3$ is $CH_3$, $R^4$ is hydrogen and $R^a$, $R^b$, $R^c$ and $R^d$ are hydrogen, which can be prepared according to the procedures described in U.S. Pat. No. 5,866,549.

Step 26b: Compound of Formula (XIII), $R^p$ is Hydrogen, $R^2$ is Hydrogen, $R^3$ is F, $R^4$ is F, $R^a$ is Hydrogen, $R^b$ is Hydrogen, $R^c$ is Hydrogen and $R^d$ is Hydrogen Compound of step 26a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 27

Compound of Formula (XIV), $R^p$ is Hydrogen, $R^2$ is Hydrogen, $R^3$ is F, $R^4$ is F, $R^a$ is Hydrogen, $R^b$ is Hydrogen, $R^c$ is Hydrogen and $R^d$ is Hydrogen Step 27a: Compound of Formula (XIV), $R^p$ is Benzoyl, $R^2$ is Hydrogen, $R^3$ is F, $R^4$ is F, $R^a$ is Hydrogen, $R^b$ is Hydrogen, $R^c$ is Hydrogen and $R^d$ is Hydrogen The title compound is prepared according to the procedures of examples 1, 2 and 10 starting from the compound of formula (XIV), wherein $R^p$ is benzoyl, $R^2$ is hydrogen, $R^3$ is $CH_3$, R is hydrogen and $R^a$, $R^b$, $R^c$ and $R^d$ are hydrogen, which can be prepared according to the procedures described in U.S. Pat. No. 5,866,549.

Step 27b: Compound of Formula (XIV), $R^p$ is Hydrogen, $R^2$ is Hydrogen, $R^3$ is F, $R^4$ is Hydrogen, $R^a$ is Hydrogen, $R^b$ is Hydrogen, $R^c$ is Hydrogen and $R^d$ is Hydrogen Compound of step 27a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 28

Compound of Formula (XI), $R^p$ is Hydrogen, Y is Hydrogen, $R^2$ is 8-quinoxaline, $R^3$ is F and $R^4$ is Hydrogen The title compound is prepared from the compound of example 20, step 20a, by following the General Experimental Procedure A for the Heck reaction.

Example 29

Compound of Formula (XII), $R^p$ is Hydrogen, Y is Hydrogen, $R^2$ is 3-quinolyl $R^3$ is F and $R^4$ is Hydrogen The title compound is prepared from the compound of example 21, step 21 a, by following the General Experimental Procedure B for the Sonagashira reaction.

Example 30

Compound of Formula (XIII), $R^p$ is hydrogen $R^2$ is 3-quinolyl, $R^3$ is F, $R^4$ is Hydrogen, $R^a$ is Hydrogen, $R^b$ is Hydrogen, $R^c$ is Hydrogen and $R^d$ is Hydrogen The title compound is prepared from the compound of example 22, step 22a, by following the General Experimental Procedure A for the Heck reaction.

Example 31

Compound of Formula (XIV), $R^p$ is Hydrogen, $R^2$ is 3-quinolyl $R^3$ is F, $R^4$ is Hydrogen $R^a$ is Hydrogen, $R^b$ is Hydrogen, $R^c$ is Hydrogen and $R^d$ is Hydrogen The title compound is prepared from the compound of example 23, step 23a, by following the General Experimental Procedure B for the Sonagashira reaction.

Example 32

Compound of Formula (XI), $R^p$ is Hydrogen, Y is Hydrogen, $R^2$ is 8-quinoxaline, $R^3$ is F and $R^4$ is F The title compound is prepared from the compound of example 24, step 24a, by following the General Experimental Procedure A for the Heck reaction.

Example 33

Compound of Formula (XII), $R^p$ is Hydrogen, Y is Hydrogen, $R^2$ is 3-quinolyl, $R^3$ is F and $R^4$ is F The title compound is prepared from the compound of example 25, step 25a, by following the General Experimental Procedure B for the Sonagashira reaction.

Example 34

Compound of Formula (XIII), $R^p$ is Hydrogen, $R^2$ is 3-quinolyl $R^3$ is F, $R^4$ is F, $R^a$ is Hydrogen, $R^b$ is hydrogen, $R^c$ is Hydrogen and $R^d$ is Hydrogen The title compound is prepared from the compound of example 26, step 26a, by following the General Experimental Procedure A for the Heck reaction.

Example 35

Compound of Formula (XIV), $R^p$ is Hydrogen, $R^2$ is 3-quinolyl, $R^3$ is F, $R^4$ is F, $R^a$ is Hydrogen, $R^b$ is Hydrogen, $R^c$ is Hydrogen and $R^d$ is Hydrogen The title compound is prepared from the compound of example 27, step 27a, by following the General Experimental Procedure B for the Sonagashira reaction.

Example 36

Compound of Formula (I), $R^p$ is Hydrogen, Y is Hydrogen, $R^1$ is Methyl, $R^3$ is Hydrogen and $R^4$ is Hydrogen Step 36a: Compound of Formula (I), $R^p$ is Benzoyl, Y is Hydrogen, $R^1$ is Methyl, $R^3$ is Hydrogen and $R^4$ is Hydrogen The title compound is prepared according to the procedures of examples 1 and 2 starting from the compound of formula (I), wherein $R^p$ is benzoyl, Y is hydrogen, $R^1$ is methyl, $R^3$ is $CH_3$ and $R^4$ is hydrogen, which can be prepared according to the procedures described in U.S. Pat. Nos. 5,561,118; 5,770,579; and 5,444,051.

Step 36b: Compound of Formula (I), $R^p$ is Hydrogen, Y is Hydrogen, $R^1$ is Methyl, $R^3$ is Hydrogen and $R^4$ is Hydrogen Compound of step 36a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 37

Compound of Formula (II), $R^p$ is Hydrogen, $R^1$ is Methyl, $R^3$ is Hydrogen, $R^4$ is Hydrogen $R^a$ is Hydrogen, $R^b$ is Hydrogen, $R^c$ is Hydrogen and $R^d$ is Hydrogen Step 36a: Compound of Formula (II), $R^p$ is Benzoyl, $R^1$ is Methyl, $R^3$ is Hydrogen, $R^4$ is Hydrogen, $R^a$ is Hydrogen, $R^b$ is Hydrogen, $R^c$ is Hydrogen and $R^d$ is Hydrogen The title compound is prepared according to the procedures of examples 1 and 2 starting from the compound of formula (II), wherein $R^p$ is benzoyl, $R^1$ is methyl, $R^3$ is CH$_3$ and $R^4$ is hydrogen, which can be prepared according to the procedures described in PCT Publication Nos. WO 93/21200 and WO 98/30574.

Step 37b: Compound of Formula (II), $R^p$ is Hydrogen $R^1$ is Methyl, $R^3$ is Hydrogen, $R^4$ is Hydrogen, $R^a$ is Hydrogen, $R^b$ is Hydrogen, $R^c$ is Hydrogen and $R^d$ is Hydrogen Compound of step 37a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 38

Compound of Formula (I), $R^p$ is Hydrogen, Y is Hydrogen, $R^1$ is Methyl, $R^3$ is —CH$_2$C=CH$_2$ and $R^4$ is Hydrogen Step 38a-1: Compound of Formula (I), $R^p$ is Benzoyl, Y is Hydrogen, $R^1$ is Methyl, $R^3$ is —CH$_2$C=CH$_2$ and $R^4$ is Hydrogen The title compound is prepared according to the procedures of examples 1 and 5 starting from the compound of formula (I), wherein $R^p$ is benzoyl, Y is hydrogen, $R^1$ is methyl, $R^3$ is CH$_3$ and $R^4$ is hydrogen, which can be prepared according to the procedures described in U.S. Pat. Nos. 5,561,118; 5,770,579; and 5,444,051.

Step 38a-2: Compound of Formula (I), $R^p$ is Benzoyl, Y is Hydrogen, $R^1$ is Methyl, $R^3$ is —CH$_2$C=CH$_2$ and $R^4$ is Hydrogen Alternatively, NaH (1.5 mmol) is added to a compound of example 36, step 36a, (1 mmol) in DMF (5 ml) at 0° C. and stirred for 30 minutes. Then allyl bromide (1.5 mmol) is added and stirred for 2–8 hrs. at 0° C. and is warmed to r.t. The reaction mixture is taken up in EtOAc and is washed with water (2x), brine (1x) and dry over Na$_2$SO$_4$. Removal of the solvent in vacuo and purification on silica gel column with 1:1 hexanes/acetone give the title compound.

Step 38b: Compound of Formula (I), $R^p$ is Hydrogen, Y is Hydrogen, $R^1$ is Methyl, $R^3$ is —CH$_2$C=CH$_2$ and $R^4$ is Hydrogen Compound of step 38a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 39

Compound of Formula (I), $R^p$ is Hydrogen, Y is Hydrogen, $R^1$ is Methyl, $R^3$ is —CH$_2$C≡CH and $R^4$ is Hydrogen Step 39a: Compound of Formula (I), $R^p$ is benzoyl, Y is hydrogen, $R^1$ is methyl, $R^3$ is —CH C=CH and $R^4$ is hydrogen To compound of example 36, step 36a, (1 mmol) in DMF (5 ml) at 0° C. is added NaH (1.5 mmol) and is stirred for 30 minutes. Then propargyl bromide (1.5 mmol) is added and stirred for 2–8 hrs. at 0° C. and is warmed to r.t. The reaction mixture is taken up in EtOAc and is washed with water (2x), brine (1x) and dry over Na$_2$SO$_4$. Removal of the solvent in vacuo and purification on silica gel column with 1:1 hexanes/acetone give the title compound.

Step 39b: Compound of Formula (I), $R^p$ is Hydrogen, Y is Hydrogen, $R^1$ is Methyl, $R^3$ is —CH$_2$C≡CH and $R^4$ is Hydrogen Compound of step 39a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 40

Compound of Formula (II), $R^p$ is Hydrogen, $R^1$ is Methyl, $R^3$ is —CH$_2$C=CH$_2$, $R^4$ is Hydrogen, $R^a$ is Hydrogen, $R^b$ is Hydrogen, $R^c$ is Hydrogen and $R^d$ is Hydrogen Step 40a-1: Compound of Formula (II), $R^p$ is Benzyol, $R^1$ is Methyl, $R^3$ is —CH$_2$C=CH$_2$, $R^4$ is Hydrogen, $R^a$ is Hydrogen, $R^b$ is Hydrogen, $R^c$ is Hydrogen and $R^d$ is Hydrogen The title compound is prepared according to the procedures of examples 1 and 5 starting from the compound of formula (II), wherein $R^p$ is benzoyl, $R^1$ is methyl, $R^3$ is CH$_3$ and R is hydrogen, which can be prepared according to the procedures described in PCT Publication Nos. WO 93/21200 and WO 98/30574.

Step 40a-2: Compound of Formula (II), $R^p$ is Benzoyl, $R^1$ is Methyl, $R^3$ is —CH$_2$C=CH$_2$, $R^4$ is Hydrogen, $R^a$ is Hydrogen, $R^b$ is Hydrogen, $R^c$ is Hydrogen and $R^d$ is Hydrogen Alternate Procedure:

To compound of example 37, step 37a, (1 mmol) in DMF (5 ml) at 0° C. is added NaH (1.5 mmol) and is stirred for 30 minutes. Then allyl bromide (1.5 mmol) is added and stirred for 2–8 hrs. at 0° C. and is warmed to r.t. The reaction mixture is taken up in EtOAc and is washed with water (2x), brine (1x) and dry over Na$_2$SO$_4$. Removal of the solvent in vacuo and purification on silica gel column with 1:1 hexanes/acetone give the title compound.

Step 40b: Compound of Formula (I), $R^p$ is Hydrogen, Y is Hydrogen, $R^1$ is Methyl, $R^3$ is —CH$_2$C=CH$_2$ and $R^4$ is Hydrogen Compound of step 40a in 5 ml of methanol is stirred at r.t. for 5 days or is heated at reflux for 24 hrs. Removal of the solvent in vacuo and purification on silica gel column with 5% MeOH/CH$_2$Cl$_2$ give the title compound.

Example 41

Compound of Formula (II), $R^p$ is Hydrogen, $R^1$ is Methyl, $R^3$ is —CH$_2$ C≡CH, $R^4$ is hydrogen, $R^a$ is hydrogen, $R^b$ is Hydrogen, $R^c$ is hydrogen and $R^d$ is Hydrogen Step 41a: Compound of Formula (11), $R^p$ is Benzoyl, $R^1$ is Methyl, $R^3$ is —CH$_2$C≡CH, $R^4$ is Hydrogen, $R^a$ is Hydrogen, $R^b$ is Hydrogen, $R^c$ is Hydrogen and $R^d$ is Hydrogen To compound of example 37, step 37a, (1 mmol) in DMF (5 ml) at 0° C. is added NaH (1.5 mmol) and is stirred for 30 minutes. Then propargyl bromide (1.5 mmol) is added and stirred for 2–8 hrs. at 0° C. and is warmed to r.t. The reaction mixture is taken up in EtOAc and is washed with water (2x), brine (1x) and dry over Na$_2$SO$_4$. Removal of the solvent in vacuo and purification on silica gel column with 1:1 hexanes/acetone give the title compound.

Step 41b: Compound of Formula (I), $R^p$ is Hydrogen, Y is Hydrogen, $R^1$ is Methyl, $R^3$ is —$CH_2C\equiv CH$ and $R^4$ is Hydrogen Compound of step 41a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 42

Compound of Formula (I), $R^p$ is Hydrogen, Y is Hydrogen, $R^1$ is Methyl, $R^3$ is —$CH_2C=CH$—(3-quinolyl) and $R^4$ is Hydrogen The title compound is prepared from the compound of example 38, step 38a, by following the General Experimental Procedure A for the Heck reaction.

Example 43

Compound of Formula (I), $R^p$ is Hydrogen, Y is Hydrogen, $R^1$ is Methyl, $R^3$ is —$CH_2C\equiv C$—(3-quinolyl) and $R^4$ is Hydrogen The title compound is prepared from the compound of example 39, step 39a, by following the General Experimental Procedure B for the Sonagashira reaction.

Example 44

Compound of Formula (II), $R^p$ is Hydrogen is Methyl, $R^3$ is —$CH_2C=CH$—(3-quinolyl), $R^4$ is Hydrogen, $R^a$ is Hydrogen, $R^b$ is Hydrogen, $R^c$ is Hydrogen and $R^d$ is Hydrogen The title compound is prepared from the compound of example 40, step 40a, by following the General Experimental Procedure A for the Heck reaction.

Example 45

Compound of Formula (II), $R^p$ is Hydrogen, $R^1$ is Methyl, $R^3$ is —$CH_2C\equiv C$—(3-quinolyl), $R^4$ is Hydrogen, $R^a$ is Hydrogen, $R^b$ is Hydrogen, $R^c$ is Hydrogen and $R^d$ is Hydrogen The title compound is prepared from the compound of example 41, step 41a, by following the General Experimental Procedure B for the Sonagashira reaction.

Example 46

Compound of Formula (I), $R^p$ is Hydrogen, Y is Hydrogen, $R^1$ is Methyl, $R^3$ is —$CH_2C=CH_9$ and $R^4$ is F Step 46a: Compound of Formula (I), $R^p$ is Benzoyl, Y is Hydrogen, $R^1$ is Methyl, $R^3$ is —$CH_2C=CH_2$ and $R^4$ is F To compound of example 38, step 38a, (1 mmol) in DMF (5 ml) at 0° C. is added NaH (2 mmol) and is stirred for 30 minutes. Then $(PhSO_2)_2NF$ (1.1 mmol) is added and stirred for 2–8 hrs. at 0° C. and is warmed to r.t. The reaction mixture is taken up in EtOAc or isopropyl acetate and is washed with water (2x), brine (1x) and dry over $Na_2SO_4$. Removal of the solvent in vacuo and purification on silica gel column with 1:1 hexanes/acetone give the title compound.

Step 46b: Compound of Formula (I), $R^p$ is Hydrogen, Y is Hydrogen, $R^1$ is Methyl, $R^3$ is —$CH_2C=CH_2$ and $R^4$ is F Compound of step 46a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 47

Compound of Formula (I), $R^p$ is Hydrogen, Y is Hydrogen, $R^1$ is Methyl, $R^3$ is —$CH_2C\equiv CH$ and $R^4$ is F Step 47a: Compound of Formula (I), $R^p$ is Benzoyl, Y is Hydrogen, $R^1$ is Methyl, $R^3$ is —$CH_2C\equiv CH$ and $R^4$ is F To compound of example 39, step 39a, (1 mmol) in DMF (5 ml) at 0° C. is added NaH (2 mmol) and is stirred for 30 minutes. Then $(PhSO_2)_2NF$ (1.1 mmol) is added and stirred for 2–8 hrs. at 0° C. and is warmed to r.t. The reaction mixture is taken up in EtOAc or isopropyl acetate and is washed with water (2x), brine (1x) and dried over $Na_2SO_4$. Removal of the solvent in vacuo and purification on silica gel column with 1:1 hexanes/acetone give the title compound.

Step 47b: Compound of Formula (I) $R^p$ is Hydrogen, Y is hydrogen, $R^1$ is Methyl $R^3$ is —$CH_2C\equiv CH$ and $R^4$ is F Compound of step 47a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 48

Compound of Formula (II), $R^p$ is Hydrogen, $R^1$ is Methyl, $R^3$ is —$CH_2C=CH_2$, $R^4$ is F, $R^a$ is Hydrogen, $R^b$ is Hydrogen, $R^c$ is Hydrogen and $R^d$ is Hydrogen Step 48a: Compound of Formula (II), $R^p$ is Benzoyl, $R^1$ is Methyl, $R^3$ is —$CH_2C\equiv CH_2$, $R^4$ is F, $R^a$ is Hydrogen, $R^b$ is Hydrogen, $R^c$ is Hydrogen and $R^d$ is Hydrogen To compound of example 40, step 40a, (1 mmol) in DMF (5 ml) at 0° C. is added NaH (2 mmol) and is stirred for 30 minutes. Then $(PhSO_2)_2NF$ (1.1 mmol) is added and stirred for 2–8 hrs. at 0° C. and is warmed to r.t. The reaction mixture is taken up in EtOAc or isopropyl acetate and is washed with water (2x), brine (1x) and dried over $Na_2SO_4$. Removal of the solvent in vacuo and purification on silica gel column with 1:1 hexanes/acetone give the title compound.

Step 48b: Compound of Formula (I), $R^p$ is Hydrogen, Y is Hydrogen, $R^1$ is Methyl, $R^3$ is —$CH_2C=CH_2$, and $R^4$ is F Compound of step 48a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 49

Compound of Formula (II), $R^p$ is Hydrogen, $R^1$ is Methyl, $R^3$ is —$CH_2C\equiv CH$ $R^4$ is Hydrogen, $R^a$ is Hydrogen, $R^b$ is Hydrogen, $R^c$ is Hydrogen and $R^d$ is Hydrogen Step 49a: Compound of Formula (II), $R^p$ is Benzoyl, $R^1$ is Methyl, $R^3$ is —$CH_2C\equiv CH$, $R^4$ is F, $R^a$ is Hydrogen, $R^b$ is Hydrogen, $R^c$ is Hydrogen and $R^d$ is Hydrogen To compound of example 41, step 41a, (1 mmol) in DMF (5 ml) at 0° C. is added NaH (2 mmol) and is stirred for 30 minutes. Then $(PhSO_2)_2NF$ (1.1 mmol) is added and stirred for 2–8 hrs. at 0° C. and is warmed to r.t. The reaction mixture is taken up in EtOAc or isopropyl acetate and is washed with water (2x), brine (1x) and dried over $Na_2SO_4$. Removal of the solvent in vacuo and purification on silica gel column with 1:1 hexanes/acetone give the title compound.

Step 49b: Compound of Formula (I), $R^p$ is Hydrogen, Y is Hydrogen, $R^1$ is Methyl $R^3$ is —$CH_2C\equiv CH$ and $R^4$ is F Compound of step 49a in 5 ml of methanol is stirred at r.t. for 5 days or is heated at reflux for 24 hrs. Removal of the solvent in vacuo and purification on silica gel column with 5% $MeOH/CH_2Cl_2$ give the title compound.

Example 50

Compound of Formula (I), $R^p$ is Hydrogen, Y is Hydrogen, $R^1$ is Methyl $R^3$ is —$CH_2C\equiv CH$—(3-quinolyl) and $R^4$ is F The title compound is prepared from the compound of example 46, step 46a, by following the General Experimental Procedure A for the Heck reaction.

Example 51

Compound of Formula (I), $R^p$ is Hydrogen, Y is Hydrogen, $R^1$ is Methyl $R^3$ is —$CH_2C\equiv C$—(3-quinolyl) and $R^4$ is F The title compound is prepared from the compound of example 47, step 47a, by following the General Experimental Procedure B for the Sonagashira reaction.

Example 52

Compound of Formula (II), $R^p$ is Hydrogen, $R^1$ is Methyl, $R^3$ is —$CH_2C\equiv CH$—(3-quinolyl) $R^4$ is F, $R^a$ is Hydrogen, $R^b$ is Hydrogen, $R^c$ is Hydrogen and $R^d$ is Hydrogen The title compound is prepared from the compound of example 48, step 48a, by following the General Experimental Procedure A for the Heck reaction.

Example 53

Compound of Formula (II), $R^p$ is Hydrogen, $R^1$ is Methyl, $R^3$ is —$CH_2C\equiv C$—(3-quinolyl), $R^4$ is F, $R^a$ is Hydrogen, $R^b$ is Hydrogen, $R^c$ is Hydrogen and $R^d$ is Hydrogen The title compound is prepared from the compound of example 49, step 49a, by following the General Experimental Procedure B for the Sonagashira reaction.

What is claimed is:
1. A compound selected from the group consisting of:

a compound of formula

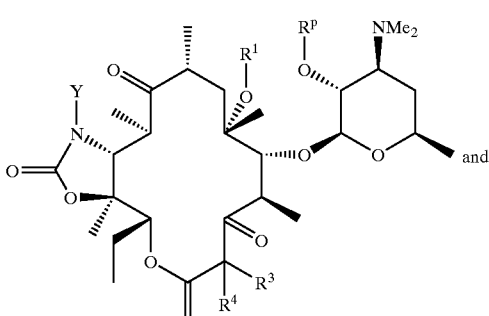

(I)

and a compound of formula

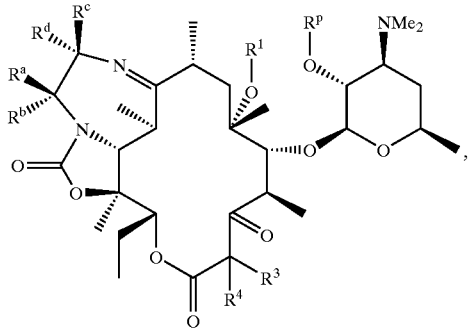

(II)

or a pharmaceutically acceptable salt thereof, wherein:
$R^p$ is hydrogen or a hydroxy protecting group;
$R^1$ is selected from the group consisting of:
  (a) $C_1$–$C_6$ alkyl substituted with one or more substituents selected from the group consisting of:
    (i) aryl;
    (ii) substituted aryl;
    (iii) heteroaryl;
    (iv) substituted heteroaryl; and
    (v) $Ar_1$–$Ar_2$, wherein $Ar_1$ and $Ar_2$ are independently selected from the group consisting of aryl, substituted aryl, heteroaryl, and substituted heteroaryl;
  (b) $C_1$–$C_6$-alkenyl-$R^2$; and
  (c) $C_1$–$C_6$-alkynyl-$R^2$;
$R^2$ is selected from the group consisting of:
  (a) aryl;
  (b) substituted aryl;
  (c) heteroaryl;
  (d) substituted heteroaryl; and
  (e) $Ar_1$–$Ar_2$, wherein $Ar_1$ and $Ar_2$ are as defined above;
$R^3$ is selected from the group consisting of:
  (a) hydrogen;
  (b) OH;
  (c) F, Cl, Br or I;
  (d) $C_1$-alkyl substituted with one or more substituents selected from the group consisting of:
    (i) aryl;
    (ii) substituted aryl;
    (iii) heteroaryl;
    (iv) substituted heteroaryl;
    (v) —NR'R", wherein R' and R" are as defined above; and
    (vi) —$OR^5$, wherein $R^5$ is hydrogen or $C_1$–$C_6$ alkyl optionally substituted with one or more substituents selected from the group consisting of:
      (1) aryl;
      (2) substituted aryl;
      (3) heteroaryl; and
      (4) substituted heteroaryl;
    (vii) —$OC(O)R^5$, wherein $R^5$ is as defined above;
  (e) $C_2$–$C_6$ alkyl optionally substituted with one or more substituents selected from the group consisting of:
    (i) aryl;
    (ii) substituted aryl;
    (iii) heteroaryl;
    (iv) substituted heteroaryl;

(v) —NR'R", wherein R' and R" are as defined above;
(vi) —OR$^5$, wherein R$^5$ is as defined above; and
(vii) —OC(O)R$^5$, wherein R$^5$ is as defined above;
(f) C$_1$–C$_6$-alkenyl;
(g) C$_1$–C$_6$-alkenyl-R$^2$, wherein R$^2$ is as defined above;
(h) C$_1$–C$_6$-alkynyl;
(i) C$_1$–C$_6$-alkynyl-R$^2$, wherein R$^2$ is as defined above;
(j) —OR$^5$, wherein R$^5$ is as defined above;
(k) —OC(O)R$^5$, wherein R$^5$ is as defined above;
(l) —CH$_2$SO$_2$NHR$^5$, wherein R$^5$ as defined above;
(m) —CH$_2$S(O)$_x$R$^5$, wherein x is 0, 1 or 2, and R$^5$ is as defined above; and
(n) —CH$_2$NHR$^5$, wherein R$^5$ as defined above;
R$^4$ is selected from the group consisting of:
(a) hydrogen;
(b) OH;
(c) NH$_2$;
(d) NHR$^5$, wherein R$^5$ is as defined above;
(e) PhSe;
(f) F, Cl, Br or I;
or R$^3$ and R$^4$ taken together with the atoms to which each is attached forms a 3- to 6-membered non-aromatic ring optionally containing a heteroatom, wherein the non-aromatic ring optionally contains one to two double bonds; or R$^3$ and R$^4$ taken together form a =CH$_2$ (exocyclic methylene), —CH$_2$O— (epoxide) or =O (oxo);
R$^a$, R$^b$, R$^c$ and R$^d$ are independently selected from the group consisting of:
(a) hydrogen;
(b) C$_1$–C$_6$ alkyl, optionally substituted with one or more substituents selected from the group consisting of:
(i) —L—M—R$^6$, wherein
L is either absent or selected from the group consisting of:
(1) —C(O)NH—;
(2) —NHC(O)—;
(3) —NH—;
(4) —N(CH$_3$)—;
(5) —O—;
(6) —S(O)$_x$—, wherein x is as defined above;
(7) —C(=NH)NH—;
(8) —NHC(NH)—;
(9) —C(O)O—;
(10) —OC(O)—;
(11) —OC(O)NH—;
(12) —NHC(O)O—; and
(13) —NHC(O)NH—;
M is absent or selected from the group consisting of:
(1) —(CH$_2$)$_l$—, wherein l is 1 to 5;
(2) —(CH$_2$)$_m$—CH=CH—, wherein m is 0 to 3;
(3) —(CH$_2$)$_n$—C≡C—, wherein n is 0 to 3;
R$^6$ is selected from the group consisting of:
(1) hydrogen;
(2) aryl;
(3) substituted aryl;
(4) heteroaryl;
(5) substituted heteroaryl; and
(6) Ar$_1$–Ar$_2$, wherein Ar$_1$ and Ar$_2$ are independently selected from the group consisting of:

(a) aryl;
(b) substituted aryl;
(c) heteroaryl; and
(d) substituted heteroaryl; and
(ii) halogen;
(c) C$_3$–C$_7$ cycloalkyl;
(d) heterocycloalkyl; and
(e) substituted heterocycloalkyl;
or any one pair of substituents selected from the group consisting of R$^a$R$^b$, R$^a$R$^c$, R$^a$R$^d$, R$^b$R$^c$, R$^b$R$^d$, and R$^c$R$^d$ taken together with the atom or atoms to which they are attached form a 3- to 7-membered ring optionally containing a hetero function selected from the group consisting of —O—; —NH—; —N(C$_1$–C$_6$ alkyl-)—; —N(aryl-C$_1$–C$_6$ alkyl-)—; —N(substituted aryl-C$_1$–C$_6$ alkyl-)—; —N(heteroaryl-C$_1$–C$_6$ alkyl-)—; —N(substituted heteroaryl-C$_1$–C$_6$ alkyl-)—; —S(O)$_x$—, wherein x is as previously defined above; —C(O)—NH—; —NH—C(O)—; —C(O)—NR$^{12}$—; and —NR$^{12}$—C(O)—; wherein R$^{12}$ is hydrogen, C$_1$–C$_3$ alkyl, C$_1$–C$_3$ alkyl substituted with aryl, substituted aryl, heteroaryl, or substituted heteroaryl; and Y is selected from the group consisting of:
(a) hydrogen;
(b) NH$_2$;
(c) OH;
(d) Z—R$^7$ wherein Z is selected from the group consisting of:
(i) —NH—(CH$_2$)$_p$—, wherein p is 0 to 5; and
(ii) —(CH$_2$)$_p$—, wherein p is 0 to 5; and
R$^7$ is selected from the group consisting of:
(i) hydrogen;
(ii) aryl;
(iii) substituted aryl;
(iv) heteroaryl;
(v) substituted heteroaryl; and
(vi) Ar$_1$–Ar$_2$, wherein Ar$_1$ and Ar$_2$ are as defined above.

2. The compound according to claim 1 having formula:

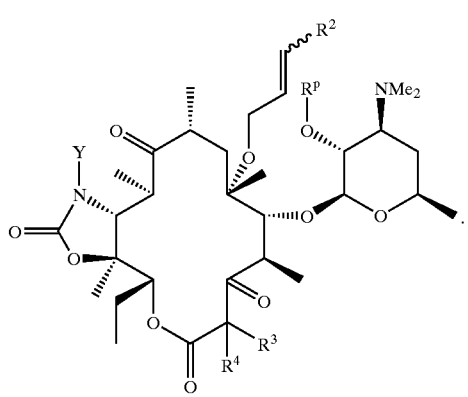

(XI)

3. The compound according to claim 1 having formula:

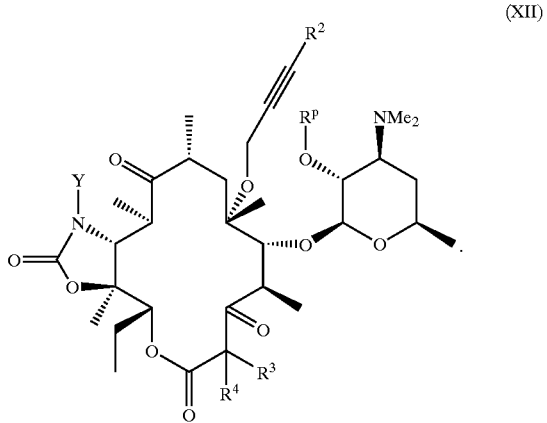

(XII)

4. The compound according to claim 1 having formula:

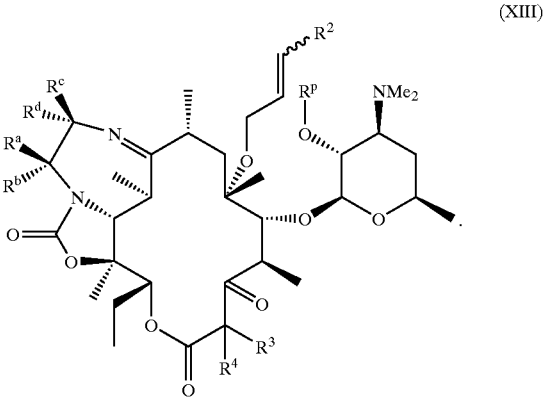

(XIII)

5. The compound according to claim 1 having formula:

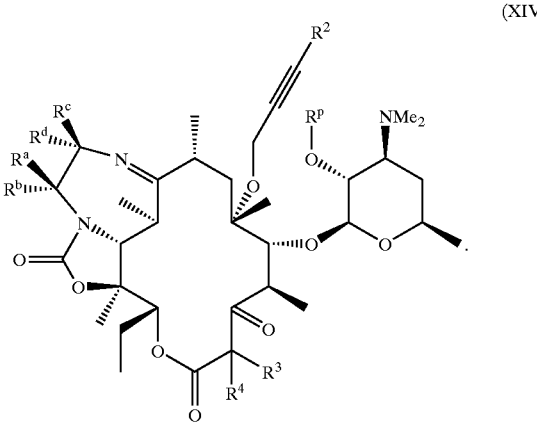

(XIV)

6. The compound according to claim 1 selected from the group consisting of:

Compound of formula (I), $R^p$ is hydrogen, Y is hydrogen, $R^1$ is —$CH_2CH(OH)CH(OH)$—(3-quinolyl), $R^3$ is —$CH_2OH$ and $R^4$ is OH;

Compound of formula (I), $R^p$ is hydrogen, Y is hydrogen, $R^1$ is methyl, $R^3$ is —$CH_2C$=CH—(3-quinolyl) and $R^4$ is hydrogen;

Compound of formula (I), $R^p$ is hydrogen, Y is hydrogen, $R^1$ is methyl, $R^3$ is —$CH_2C$≡C—(3-quinolyl) and $R^4$ is hydrogen;

Compound of formula (II), $R^p$ is hydrogen, $R^1$ is methyl, $R^3$ is —$CH_2C$=CH—(3-quinolyl), $R^4$ is hydrogen, $R^a$ is hydrogen, $R^b$ is hydrogen, $R^c$ is hydrogen and $R^d$ is hydrogen;

Compound of formula (II), $R^p$ is hydrogen, $R^1$ is methyl, $R^3$ is —$CH_2C$≡C—(3-quinolyl), $R^4$ is hydrogen, $R^a$ is hydrogen, $R^b$ is hydrogen, $R^c$ is hydrogen and $R^d$ is hydrogen;

Compound of formula (I), $R^p$ is hydrogen, Y is hydrogen, $R^1$ is methyl, $R^3$ is —$CH_2C$=CH—(3-quinolyl) and $R^4$ is F;

Compound of formula (I), $R^p$ is hydrogen, Y is hydrogen, $R^1$ is methyl, $R^3$ is —$CH_2C$≡C—(3-quinolyl) and $R^4$ is F;

Compound of formula (II), $R^p$ is hydrogen, $R^1$ is methyl, $R^3$ is —$CH_2C$=CH—(3-quinolyl), $R^4$ is F, $R^a$ is hydrogen, $R^b$ is hydrogen, $R^c$ is hydrogen and $R^d$ is hydrogen; and Compound of formula (II), $R^p$ is hydrogen, $R^1$ is methyl, $R^3$ is —$CH_2C$≡C—(3-quinolyl), $R^4$ is F, $R^a$ is hydrogen, $R^b$ is hydrogen, $R^c$ is hydrogen and $R^d$ is hydrogen.

7. A pharmaceutical composition comprising a compound according to claim 1 and a pharmaceutically acceptable carrier.

8. A method of treating a bacterial infection comprising administering a therapeutically effective amount of a compound according to claim 1 to a patient in need of such treatment.

9. The compound according to claim 2 selected from the group consisting of:

Compound of formula (XI), $R^p$ is benzoyl, Y is hydrogen, $R^2$ is 3-quinolyl, $R^3$ and $R^4$ taken together is =$CH_2$;

Compound of formula (XI), $R^p$ is hydrogen, Y is hydrogen, $R^2$ is 3-quinolyl, $R^3$ is hydrogen and $R^4$ is hydrogen;

Compound of formula (XI), $R^p$ is hydrogen, Y is hydrogen, $R^2$ is 3-quinolyl, $R^3$ is —$CH_2CH$=$CH_2$ and $R^4$ is hydrogen;

Compound of formula (XI), $R^p$ is hydrogen, Y is hydrogen, $R^2$ is 3-quinolyl, $R^3$ is —$CH_2CH(CO_2Me)_2$ and $R^4$ is hydrogen;

Compound of formula (XI), $R^p$ is hydrogen, Y is hydrogen, $R^2$ is 3-quinolyl, $R^3$ and $R^4$ taken together is —$CH_2O$—;

Compound of formula (XI), $R^p$ is hydrogen, Y is hydrogen, $R^2$ is 3-quinolyl, $R^3$ is F and $R^4$ is hydrogen;

Compound of formula (XI), $R^p$ is hydrogen, Y is hydrogen, $R^2$ is 3-quinolyl, $R^3$ is F and $R^4$ is F;

Compound of formula (XI), $R^p$ is hydrogen, Y is hydrogen, $R^2$ is 3-quinolyl, $R^3$ is —$CH_2F$ and $R^4$ is F;

Compound of formula (XI), $R^p$ is hydrogen, Y is hydrogen, $R^2$ is 8-quinoxaline, $R^3$ is F and $R^4$ is hydrogen; and Compound of formula (XI), $R^p$ is hydrogen, Y is hydrogen, $R^2$ is 8-quinoxaline, $R^3$ is F and $R^4$ is F.

10. The compound according to claim 3 selected from the group consisting of:

Compound of formula (XII), $R^p$ is hydrogen, Y is hydrogen, $R^2$ is 3-quinolyl, $R^3$ is hydrogen and $R^4$ is hydrogen;

Compound of formula (XII), $R^p$ is hydrogen, Y is hydrogen, $R^2$ is 3-quinolyl, $R^3$ is F and $R^4$ is hydrogen;

Compound of formula (XII), $R^p$ is hydrogen, Y is hydrogen, $R^2$ is 3-quinolyl, $R^3$ is F and $R^4$ is F.

11. The compound according to claim 4 selected from the group consisting of:

Compound of formula (XIII), $R^p$ is hydrogen, $R^2$ is 3-quinolyl, $R^3$ is hydrogen, $R^4$ is hydrogen, $R^a$ is hydrogen, $R^b$ is hydrogen $R^c$ is hydrogen and $R^d$ is hydrogen;

Compound of formula (XIII), $R^p$ is hydrogen, $R^2$ is 3-quinolyl, $R^3$ is F, $R^4$ is hydrogen, $R^a$ is hydrogen, $R^b$ is hydrogen $R^c$ is hydrogen, and $R^d$ is hydrogen; and Compound of formula (XIII), $R^p$ is hydrogen, $R^2$ is 3-quinolyl, $R^3$ is F, $R^4$ is F, $R^a$ is hydrogen, $R^b$ is hydrogen, $R^c$ is hydrogen, and $R^d$ is hydrogen.

12. The compound according to claim 5 selected from the group consisting of:

Compound of formula (XIV), $R^p$ is hydrogen, $R^2$ is 3-quinolyl, $R^3$ is hydrogen, $R^4$ is hydrogen, $R^a$ is hydrogen $R^b$ is hydrogen $R^c$ is hydrogen and $R^d$ is hydrogen;

Compound of formula (XIV), $R^p$ is hydrogen, $R^2$ is 3-quinolyl, $R^3$ is F, $R^4$ is hydrogen, $R^a$ is hydrogen, $R^b$ is hydrogen $R^c$ is hydrogen, and $R^d$ is hydrogen; and Compound of formula (XIV), $R^p$ is hydrogen, $R^2$ is 3-quinolyl, $R^3$ is F, $R^4$ is F, $R^a$ is hydrogen, $R^b$ is hydrogen, $R^c$ is hydrogen, and $R^d$ is hydrogen.

* * * * *

UNITED STATES PATENT AND TRADEMARK OFFICE
CERTIFICATE OF CORRECTION

PATENT NO.     : 6,569,836 B2
DATED          : May 27, 2003
INVENTOR(S)    : Ly Tam Phan et al.

It is certified that error appears in the above-identified patent and that said Letters Patent is hereby corrected as shown below:

Column 57,
Line 12, replace "$R^5$ as defined" with -- $R^5$ is as defined --.
Line 50, replace "NHC(NH)-;" with -- NHC(=NH)-; --.

Signed and Sealed this

Ninth Day of September, 2003

JAMES E. ROGAN
*Director of the United States Patent and Trademark Office*